:

US009502665B2

(12) United States Patent
Melucci et al.

(10) Patent No.: US 9,502,665 B2
(45) Date of Patent: *Nov. 22, 2016

(54) ORGANIC SEMICONDUCTOR MATERIAL

(71) Applicant: E.T.C. S.R.L., Bologna (IT)

(72) Inventors: Manuela Melucci, Bologna (IT); Laura Favaretto, Ozzano dell'Emilia (IT); Massimo Zambianchi, Cesena (IT); Raffaella Capelli, Bologna (IT); Michele Muccini, Bologna (IT)

(73) Assignee: E.T.C. S.R.L., Bologna (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/435,411

(22) PCT Filed: Nov. 14, 2013

(86) PCT No.: PCT/IB2013/060128
§ 371 (c)(1),
(2) Date: Apr. 13, 2015

(87) PCT Pub. No.: WO2014/076650
PCT Pub. Date: May 22, 2014

(65) Prior Publication Data
US 2015/0236270 A1 Aug. 20, 2015

(30) Foreign Application Priority Data

Nov. 15, 2012 (IT) .............................. MI2012A1939

(51) Int. Cl.
*C07D 495/04* (2006.01)
*H01L 51/00* (2006.01)
*C09K 11/06* (2006.01)
*H01L 51/05* (2006.01)
*H01L 51/52* (2006.01)

(52) U.S. Cl.
CPC ......... *H01L 51/0071* (2013.01); *C07D 495/04* (2013.01); *C09K 11/06* (2013.01); *H01L 51/0068* (2013.01); *C09K 2211/1037* (2013.01); *H01L 51/0545* (2013.01); *H01L 51/0558* (2013.01); *H01L 51/5296* (2013.01); *H01L 2251/308* (2013.01)

(58) Field of Classification Search
CPC C07D 207/12; C07D 409/04; C07D 205/04; C07D 207/08; C07D 207/10
USPC .................................... 548/400, 453; 257/40
See application file for complete search history.

(56) References Cited

U.S. PATENT DOCUMENTS

| 5,276,009 A | 1/1994 | Muenster et al. |
| 2015/0214488 A1* | 7/2015 | Melucci ............. H01L 51/0068 257/40 |
| 2015/0287932 A1* | 10/2015 | Zambianchi ......... C07D 495/04 257/40 |
| 2015/0311448 A1* | 10/2015 | Melucci ............... C07D 495/04 257/40 |

FOREIGN PATENT DOCUMENTS

| DE | 1954550 | 7/1971 |
| EP | 0467206 | 1/1992 |
| FR | 2066727 | 8/1971 |
| JP | 2009/099942 | 5/2009 |
| WO | 2006094292 | 9/2006 |
| WO | 2008127029 | 10/2008 |
| WO | 2010/131764 | 11/2010 |

OTHER PUBLICATIONS

Melucci, M., M. Zambianchi, L. Favaretto, M. Gazzano, a. Zanelli, M. Monari, R. Capelli, S. Troisi, S. Toffanin, and M. Muccini "Thienopyrrolyl dione end-caped oligothiophene ambipolar semiconductors for thin film- and light emitting transistors" Chem. Comm. (2011), 47: pp. 11840-11842.*
Bijleveld, Johan C. et al. "Poly(diketopyrrolopyrrole-terthiophene) for Ambipolar Logic and Photovoltaics" J.Am.Chem.Soc. (2009), 131, pp. 16616-16617.
Sonar, Prashant. et al "A Low-Bandgap Diketopyrrolopyrrole-Benzothiadiazole-Based Copolymer for High-Mobility Ambipolar Organic Thin-Film Transistors" Mater. (2010), 22, 47, pp. 5409-5413.
Yoon, Myung-Han et al. "Organic Thin-Film Transistors Based on Carbonyl-Functionalized Quaterthiophenes: High Mobility N-Channel Semiconductors and Ambipolar" Transport J. Am. Chem. Soc.( 2005), 127, pp. 1348-1349.
Facchetti, Antonio et al. "Building Blocks for n-Type Organic Electronics: Regiochemically Modulated Inversion of Majority Carrier Sign in Perfluoroarene-Modified Polythiophene Semiconductors" Angew. Chem. Int. Ed. (2003), 42, pp. 3900-3903.
Letizia, Joseph A. et al. "n-Channel Polymers by Design: Optimizing the Interplay of Solubilizing Substituents, Crystal Packing, and Field-Effect Transistor Characteristics in Polymeric Bithiophene-Imide Semiconductors" J. Am. Chem. Soc. (2008), 130, pp. 9679-9694.
Zhang, Qing T. et al. Alternating Donor/Acceptor Repeat Units in Polythiophenes.Intramolecular Charge Transfer for Reducing Band Gaps in Fully Substituted Conjugated PolymersJ.Am.Chem.Soc. (1998) 120, 5355-5362.
Pomerantz, Martin "Planar 2,2-bithiophenes with 3,3- and 3,3,4,4-substituents. A computational study" Tetrahedron Letters 44 (2003) pp. 1653-1565.
Nielsen, Christian B. "New Regiosymmetrical Dioxopyrroloand Dihydropyrrolo-Functionalized Polythiophenes" Organic Letters (2004), 6, 19, 3381-3384.
Wei Hong et al, "Linear fused dithieno [2,3-b: 3 '2'-d]thiophene diimides" Organic Letters, vol. 13, No. 6 (2011), pp. 1410-1413.
Ronova, Iga A et al: "The effect of conformational rigidity on the initial decomposition temperature of some heterocyclic polymides", High Performance Polymers, Institute of Physics Publishing, Bristol GB, vol. 14, No. 2 (2002) pp. 195-208.

(Continued)

*Primary Examiner* — Alicia L Otton
*Assistant Examiner* — Sagar Patel
(74) *Attorney, Agent, or Firm* — Steinfl & Bruno, LLP

(57) ABSTRACT

Compounds useful as organic semiconductor materials, and semiconductor devices containing such organic semiconductor materials are described.

6 Claims, 11 Drawing Sheets

(56) References Cited

OTHER PUBLICATIONS

Gaina C. et al, "Polyimides containing 1,4-dithiine units and their corresponding thiophene 2,3,4,5 tetracarboxylimide units" High Performance Polymers, Institute of physics publishing, Bristol GB, vol. 11, No. 2 (1999) pp. 185-195.
Melucci, Manuela et al: 11 Thienopyrrolyl 1-15 di one end-capped oligothiophene ambipolar semiconductors for thin film-and light emitting transistors 11 , Chemical Communications, vol. 47, No. 43, 21 (2011) pp. 11840-11842.
Melucci, Manuela "A bright future for organic field-effect transistors", Nature Materials, vol. 5, No. 8, 1 (2006), pp. 605-613.
PCT International Search Report mailed on Dec. 13, 2013 for PCT/IB2013/059200 filed on Oct. 8, 2013 in the name of E.T.C. S.R.L.
PCT Written Opinion mailed on Dec. 13, 2013 for PCT/IB2013/059200 filed on Oct. 8, 2013 in the name of E.T.C. S.R.L.
PCT International Search Report mailed on Jan. 7, 2014 for PCT/IB2013/060128 filed on Nov. 14, 2013 in the name of E.T.C. S.R.L.
PCT Written Opinion of the International Searching Authority mailed on Jan. 7, 2014 for PCT/IB2013/060128 filed on Nov. 14, 2013 in the name of E.T.C. S.R.L.
PCT Written Opinion of the International Preliminary Examining Authority mailed on Nov. 3, 2014 for PCT/IB2013/060128 filed on Nov. 14, 2013 in the name of E.T.C. S.R.L.
PCT International Preliminary Report of Patentability mailed on Jan. 23, 2015 for PCT/IB2013/060128 filed on Nov. 14, 2013 in the name of E.T.C. S.R.L.
International Search Report issued on Jan. 29, 2014 for PCT/IB2013/060162 which was filed on Nov. 15, 2013 in the name of E.T.C. S.R.L.
Written Opinion issued on Jan. 29, 2014 for PCT/IB2013/060162 which was filed on Nov. 15, 2013 in the name of E.T.C. S.R.L.

\* cited by examiner

ORGANIC SEMICONDUCTOR MATERIAL

CROSS REFERENCE TO RELATED APPLICATIONS

The present application is the US national stage of International Patent Application PCT/IB2013/060128 filed internationally on Nov. 14, 2013 which, in turn, claims priority to Italian Patent Application No. MI2012A001939 filed on Nov. 15, 2012.

The present invention relates to a novel ambipolar organic semiconductor material, and semiconductor devices containing said ambipolar organic semiconductor material.

It is known that organic semiconductors are materials into which charge can be reversibly introduced by the application of electromagnetic energy or chemical dopants. The electronic conductivity of these materials lies between that of metals and insulators, spanning a broad range of $10^{-9}$ to $10^3$ $\Omega^{-1}$ $cm^{-1}$. As in traditional inorganic semiconductors, organic materials can function either as p-type or n-type. In p-type semiconductors the majority carriers are holes, while in n-type the majority carriers are electrons.

The vast majority of the prior art has focused on the design, synthesis, and structure-property relationships of p-type organic semiconductor materials, including: oligoacenes, fused oligothiophenes, anthradithiophenes, carbazoles, oligophenylenes, and oligofluorenes, some of which have resulted in field-effect transistors with performance superior to amorphous silicon. In contrast, the development of n-type and ambipolar oligomer and polymer semiconductors has lagged behind p-type materials. In fact, compared to the p-type semiconductors, n-type and ambipolar semiconductors are still not fully developed, and the performances are not satisfactory. Materials with n-type and ambipolar charge transport are highly desirable to realize complementary integrated circuits and integrated organic devices such as light emitting transistors, leading to flexible, large-area, and low-cost electronic applications.

A variety of organic semiconductors have been considered in the art as n-type organic semiconductor materials.

Aromatic tetracarboxylic anhydride and their diimide derivatives were reported among the first n-channel materials. Among the materials of this class, perylenetetracarboxylic diimides having fluorinated side chains showed mobilities up to 0.72 $cm^2V^{-1}s^{-1}$, which only slightly decreased upon air exposure. Air stability, packing grain size and morphology of the deposited films as well as electrical performance can be altered by varying side-chain length, insertion of oxygenated groups and degree of fluorination. However, most of the perylene building blocks, due to the structural rigidity and moderate solubility, do not allow readily structural changes limiting the volume of materials accessible.

Other classes of n-type organic materials have been described such as cyanovinyl oligomers, fullerenes.

J. Am. Chem. Soc. 2009, 131, 16616-16617 describes ambipolar charge transport properties of diketopyrrolopyrrole-copolymers.

A benzothiadiazole-diketopyrrolopyrrole copolymer described in Mater. 2010, 22, 47, 5409-5413, shows high and balanced hole- and electron mobilities of 0.35 $cm^2$ $V^{-1}s^{-1}$ and 0.40 $cm^2V^{-1}s^{-1}$, respectively. Larger electron mobilities values up to 0.85 $cm^2V^{-1}s^{-1}$ were achieved in air for electron-only transporting n-type polymer, called poly{[N,N9-bis(2-octyldodecyl)-naphthalene-1,4,5,8-bis(dicarboximide)-2,6-diyl]-alt-5,59-(2,29-bithiophene)}, (Polyera Activink N2200), in a staggered top gate configuration.

N-type semiconductor materials consisting of oligothiophenes bearing fluorinated side groups have been also described in J. Am. Chem. Soc. 2005, 127, 1348 and Angew. Chem. Int. Ed. 2003, 42, 3900. These oligomers showed mobilities up to 0.43 $cm^2V^{-1}s^{-1}$. However, OFETs based on most of these perfluoroaryl and perfluoroalkylaryl substituted materials were unstable in air or suffered from high threshold voltage. Fluorocarbonyl-functionalized oligomers were also described, which showed improved air stability, but lower electron mobilities with respect to fluorinated oligomers.

Oligomers and polymers containing a bithiophene-imide units as inner core have also been described.

For example, J. Am. Chem. Soc. 2008, 130, 9679-9694 describes N-alkyl-2,2'-bithiophene-3,3'-dicarboximide-based homopolymers and copolymers showing p-type or n-type semiconductor behavior depending on the polymeric structure. However, no air-stable devices could be achieved with such materials. In addition, the poor reactivity of the starting dihalogenated bithiophene-imide compounds limits the accessibility of this class of materials.

J. Am. Chem. Soc. 1998, 120, 5355-5362, Tetrahedron Letters 44 (2003)1563-1565 disclose copolymers containing electron poor 3,4-imido-thienyl blocks alternated to electron rich amino substituted thienyl blocks. No investigation was performed regarding the electrical properties of such copolymers.

N-alkylated poly(dioxopirrolothiophene)s are described in Organic Letters 2004, 6, 19, 3381-3384. However, no proof of an efficient n-type behavior in OFET devices is reported.

Each of the afore mentioned class of materials has poor electrical performances.

WO2008/127029 relates to dioxypirrolo-heterocyclic compounds having the pyrrole moiety fused to the 3,4 position of the thienyl ring and organic electronic devices using said dioxypirrolo-heterocyclic compounds.

Wei Hong et al, "Linear fused dithieno [2,3-b: 3'2'-d] thiophene diimides" Organic Letters, vol 13, no. 6, 18 Mar. 2011, pages 1420-1413, discloses a class of linear fully fused dithieno thiophene diimides.

The documents: DE1954550; Ronova Iga A et al: "The effect of conformational rigidity on the initial decomposition temperature of some heterocyclic polyimides", High Performance Polymers, Institute of Physics Publishing, Bristol G B, vol. 14, No. 2, 1 Jan. 2002, pages 195-208; and Gaina C. et al, "Polyimides containing 1,4-dithiine units and their corresponding thiophene 2,3,4,5 tetracarboxylimide units" High Performance Polymers, Institute of physics publishing, Bristol G B, vol. 11, No. 2, 1 Jun. 1999, pages 185-195, disclose polymeric diimmide compounds in which the member connecting the polymer repeating units is the N-imidic substituent. The three last cited documents do not mention any semiconductor property of the compounds therein disclosed.

WO2006/094292 discloses thienopyridine compounds capable of modulating the stability and/or activity of hypoxia inducible factor, pharmaceutical compositions comprising said compounds and chemical intermediates useful for preparing said compounds. Among said chemical intermediates, specific compounds having a 4,6-dioxo-thieno[2,3-c]pyrrole nucleus are disclosed.

EP0467206 discloses specific compounds having a 4,6-dioxo-thieno[2,3-c]pyrrole nucleus and their use as herbicide.

However, WO2006/094292 and EP0467206 do not teach the semiconductor properties of said compounds.

Therefore, there is still the need of n-type organic semiconductor materials or compounds that possess higher electron mobility properties.

In the present specification and in the claims, the term "n-type organic semiconductor" means a material that, inserted as active layer in a field effect device architecture with a source, a drain and gate control electrodes, shows an electron mobility higher than $10^{-7}$ cm$^2$V$^{-1}$s$^{-1}$.

It is an object of the present invention to provide new organic materials suitable for use as semiconductor material which is free from said disadvantages. Said object is achieved with compounds whose main features are disclosed in the first claim, a use of said compound whose main features are disclosed in claim 10 and an electronic device whose main features are disclosed in claim 13. Other features of said compound are disclosed in claims 2 to 9.

Advantageously, the compounds according to the present invention may be useful as p-type, n-type or ambipolar organic semiconductor material.

Particularly, the compounds according to the present invention possess high electron mobility properties, excellent stability under atmospheric conditions and are accessible through synthetically easy processes.

In addition, most of the compounds according to the present invention are provided with electroluminescence, in addition to the above mentioned ambipolar charge transport properties. This is of crucial interest for the realization of advanced single layer ambipolar organic light emitting transistors (OLET) with low manufacturing costs.

Further advantages and features of the compounds, materials and devices according to the present invention will become clear to those skilled in the art from the following detailed and non-limiting description of an aspect thereof with reference to the attached drawings, wherein:

FIGS. 1(a) and (b) show absorption and emission spectra of a compound 6 according to the present invention in CH$_2$Cl$_2$ solution and 30 nm thick vacuum sublimed film;

Figure 5:
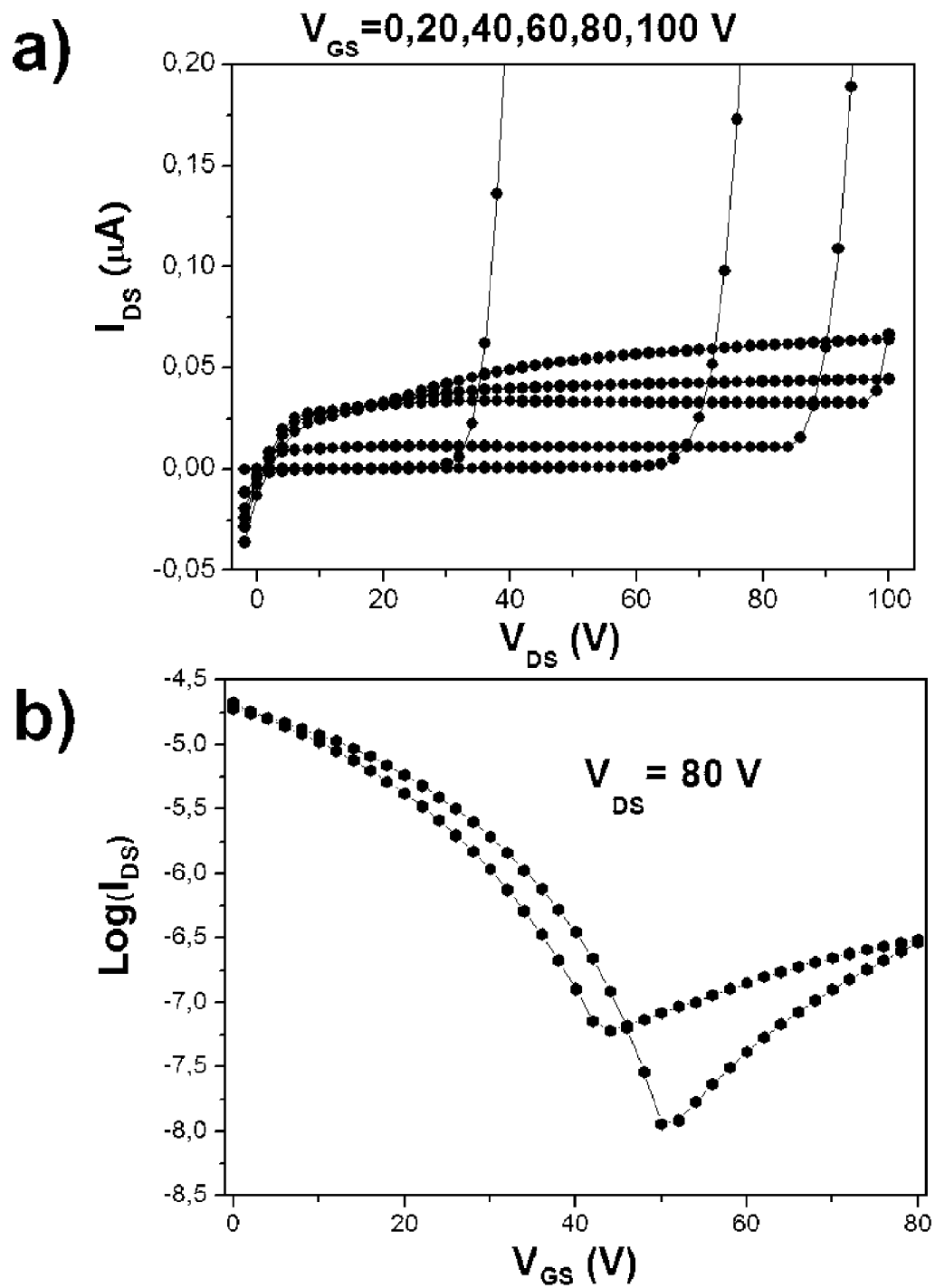
Figure 6:
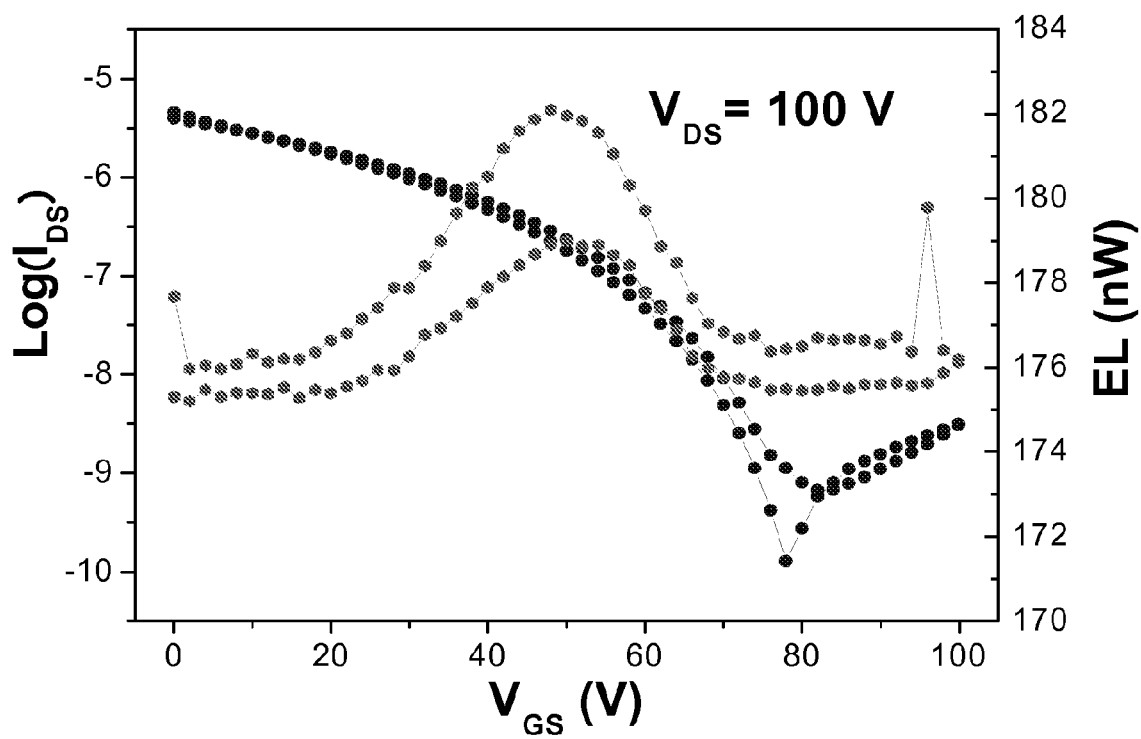
Figure 7:
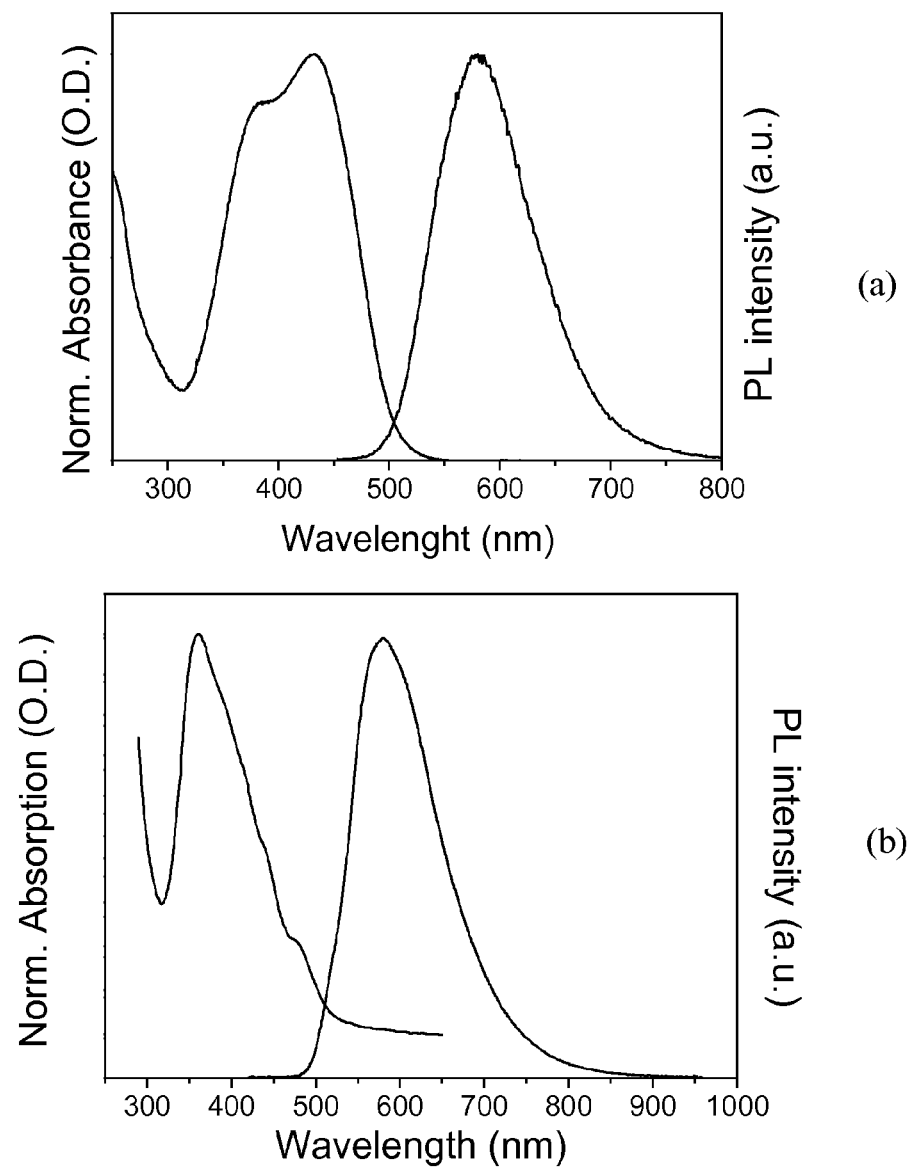
Figure 8:
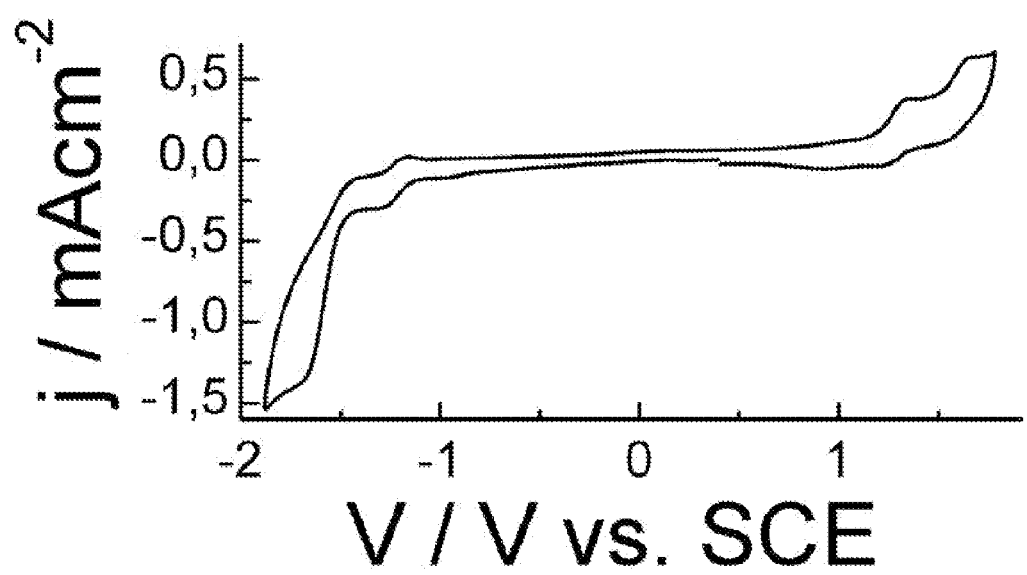
Figure 9:
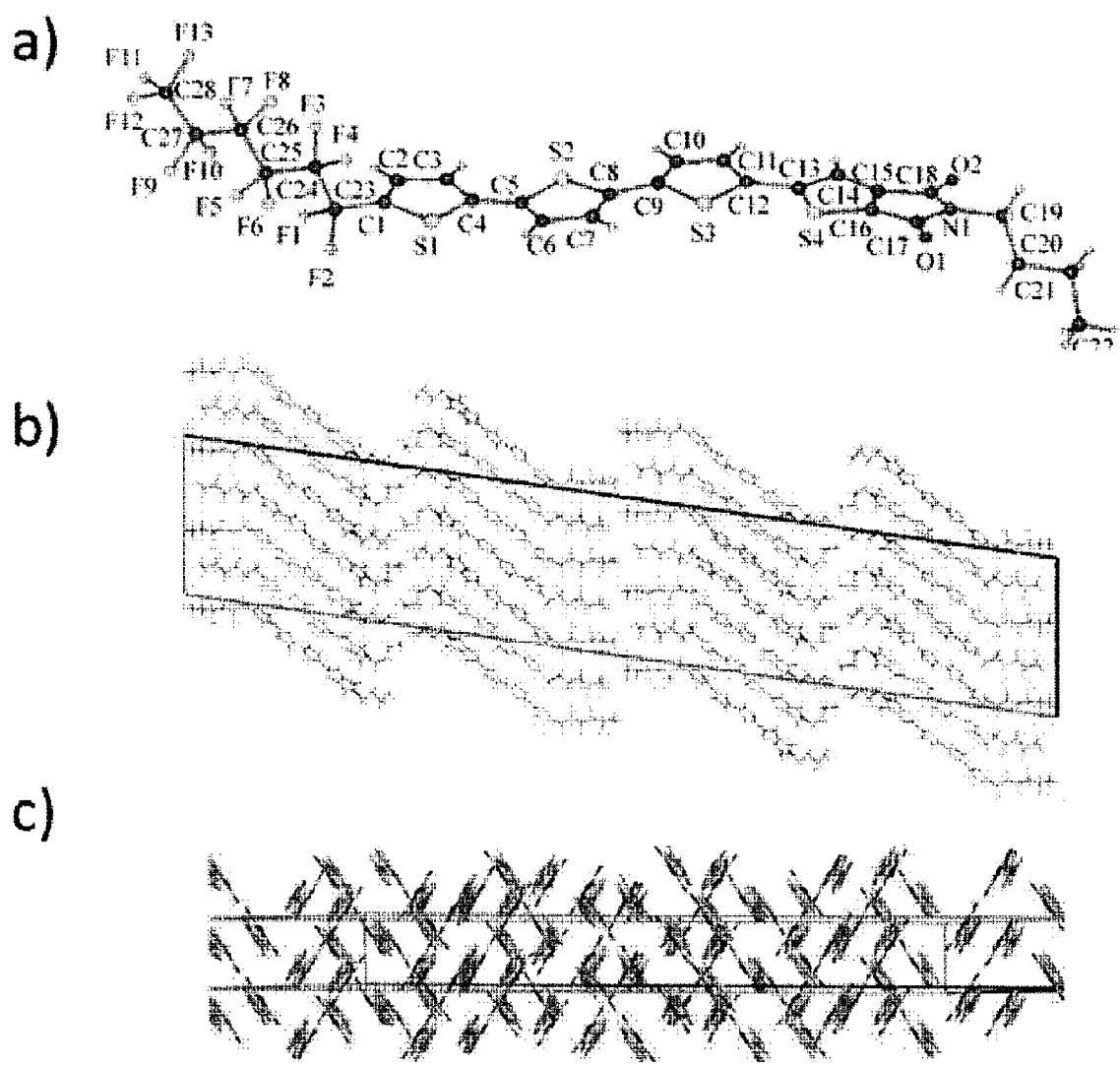

FIGS. 5(a) and (b) show electrical characteristics for OTFTs comprising a 30 nm thick film of compound 6;

FIG. 6 shows opto-electronic transfer curves of an OLET device;

FIGS. 7(a) and (b) show absorption and emission spectra of a compound 8 according to the present invention in CH$_2$Cl$_2$ solution and 30 nm thick vacuum sublimed film;

FIG. 8 shows a cyclic voltammetry of a preferred compound 8 according to the present invention;

FIGS. 9(a), (b) and (c) show, respectively, crystal structure of a compound 8 according to the invention; herringbone-like packing view down the b axis; and herringbone-like packing view down the long molecular axis; wherein the H atoms the perfluorohexyl and n-butyl chain have been removed for clarity.

Figure 10:
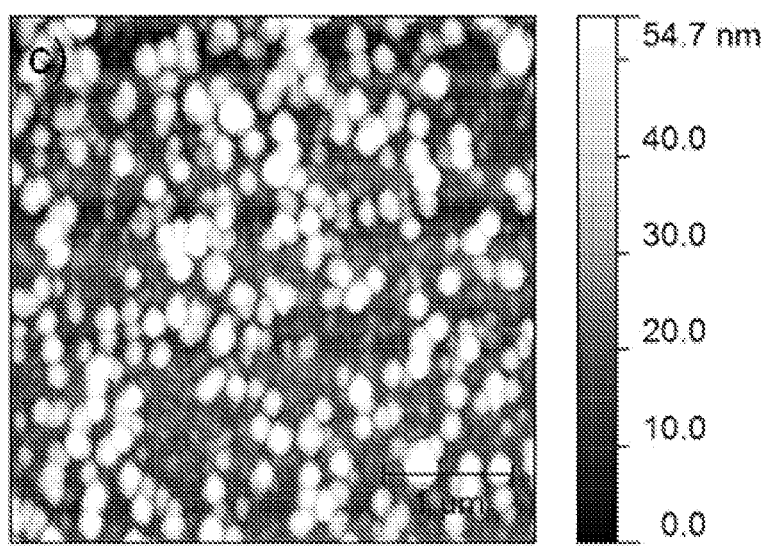
Figure 11:
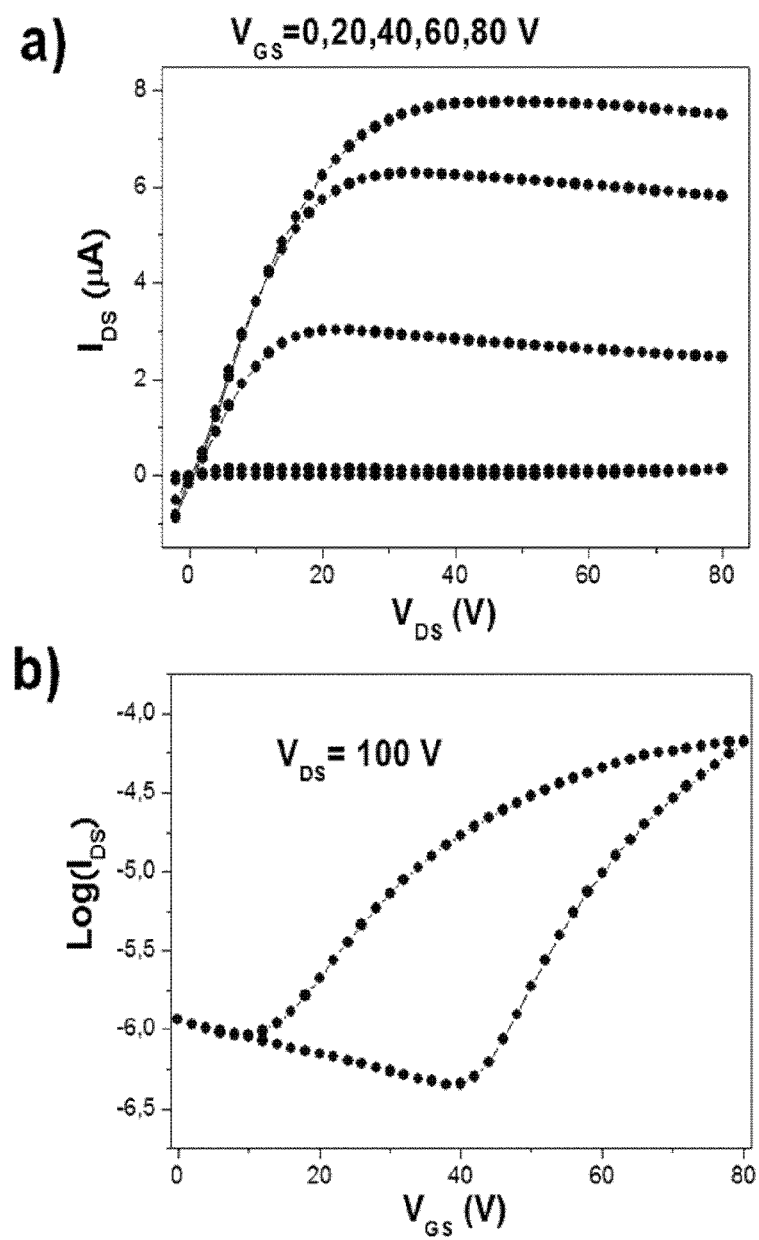
Figure 12:
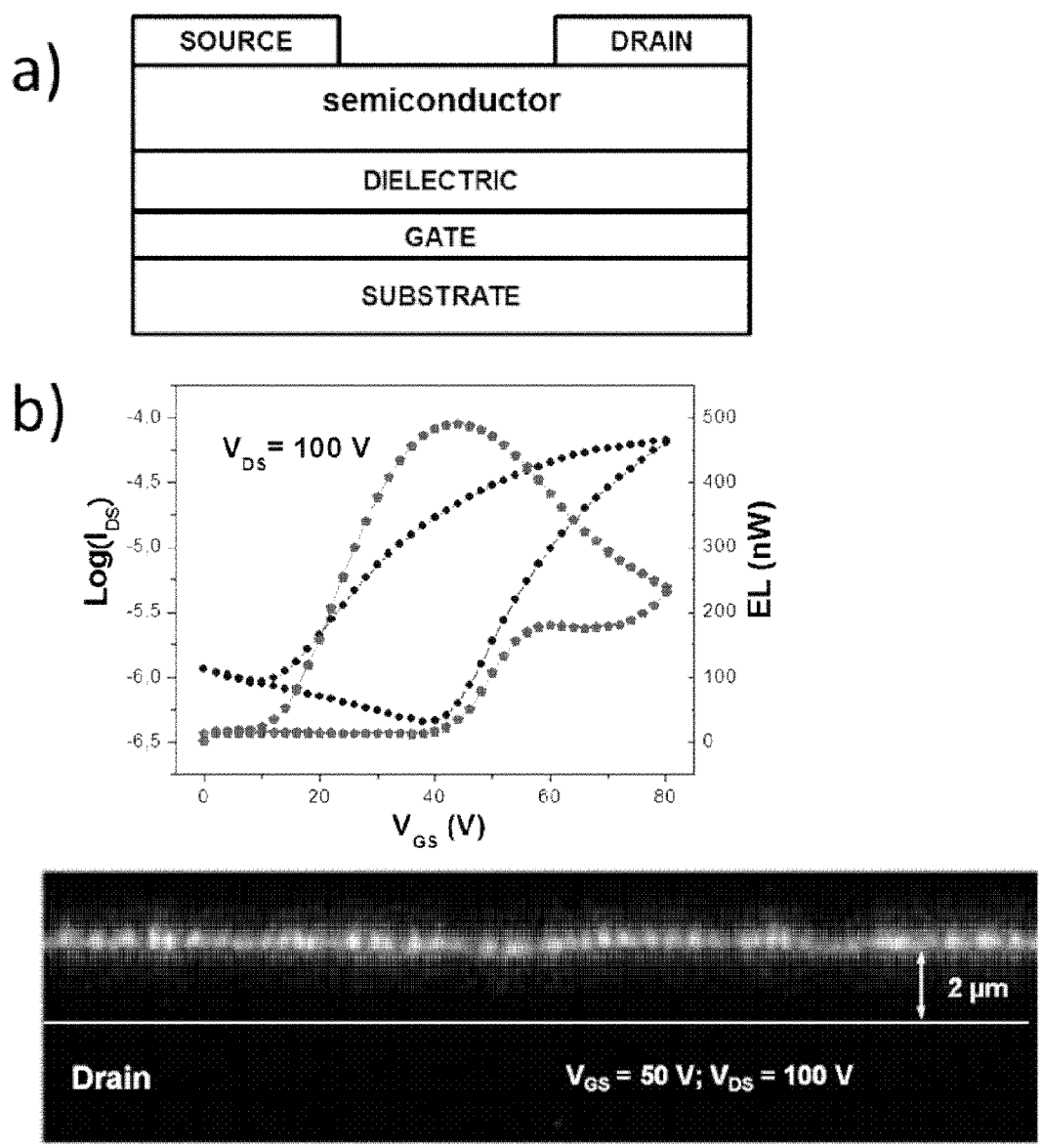

FIG. 10 shows Atomic Force images of a 30 nm thick film of compound 8 according to the present invention, grown on PMMA;

FIGS. 11(a) and (b) show electrical characteristics for OTFTs comprising a 30 nm thick film of compound 8;

FIGS. 12(a), (b) and (c) show a schematic view, optoelectronic transfer curves and an optical microscope image of a working OLET device comprising a 30 nm thick film of compound 8.

According to an aspect of the present invention, a compound of formula (I) or (II) is provided:

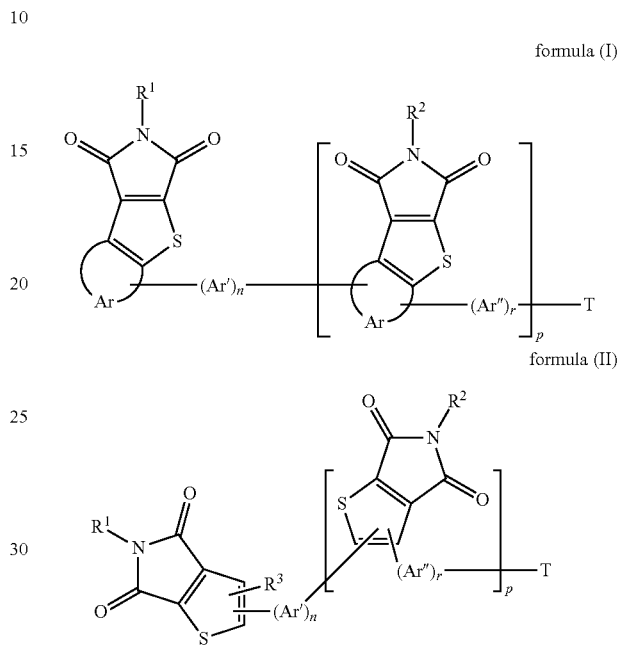

formula (I)

formula (II)

wherein:

R$^1$, R$^2$ independently of each other, are selected in the group consisting of hydrogen, C$_1$-C$_{40}$ linear or branched alkyl groups, C$_2$-C$_{40}$ linear or branched alkenyl groups, C$_2$-C$_{40}$ linear or branched alkynyl groups, C$_1$-C$_{40}$ linear or branched heteroalkyl groups, C$_2$-C$_{40}$ linear or branched heteroalkynyl groups, C$_2$-C$_{40}$ linear or branched heteroalkynyl groups, C$_3$-C$_{40}$ linear or branched cycloalkyl groups, C$_2$-C$_{40}$ heterocycloalkyl groups, C$_2$-C$_{40}$ linear or branched alkylcarboxylic groups, C$_2$-C$_{40}$ linear or branched alkylcarboxamide groups, C$_2$-C$_{40}$ linear or branched alkylimino groups, C$_1$-C$_{40}$ linear or branched alkylsulphonic groups, C$_1$-C$_{40}$ linear or branched alkyl nitrile groups;

Ar, Ar', Ar'', independently of each other, are selected in the group consisting of monocyclic aryl groups, substituted monocyclic aryl groups, polycyclic aryl groups, substituted polycyclic aryl groups, monocyclic heteroaryl groups, substituted monocyclic heteroaryl groups, polycyclic heteroaryl groups, substituted polycyclic heteroaryl groups and combinations thereof as dimers, trimers and tetramers;

R$^3$ is selected in the group consisting of hydrogen, halogen, C$_1$-C$_{20}$ linear or branched alkyl groups, C$_2$-C$_{20}$ linear or branched alkenyl groups, C$_2$-C$_{20}$ linear or branched alkynyl groups, C$_1$-C$_{20}$ linear or branched heteroalkyl groups, C$_2$-C$_{20}$ linear or branched heteroalkenyl groups, C$_2$-C$_{20}$ linear or branched heteroalkynyl groups, C$_3$-C$_{20}$ linear or branched cycloalkyl groups, C$_2$-C$_{20}$ heterocycloalkyl groups, C$_2$-C$_{20}$ linear or branched alkylcarboxylic groups, C$_2$-C$_{20}$ linear or branched alkylcarboxamide groups, C$_2$-C$_{20}$ linear or branched alkylimino groups, C$_1$-C$_{20}$ linear or branched alkylsulphonic groups, C$_1$-C$_{20}$ linear or branched alkyl nitrile groups;

n, r, independently of each other, are integers between 1 and 50;

p is an integer between 0 and 5; and

T is a terminal unit of the compound and is selected among $C_1$-$C_{40}$ linear or branched alkyl groups, $C_2$-$C_{40}$ linear or branched alkenyl groups, $C_2$-$C_{40}$ linear or branched alkynyl groups, $C_1$-$C_{40}$ linear or branched heteroalkyl groups, $C_2$-$C_{40}$ linear or branched heteroalkenyl groups, $C_2$-$C_{40}$ linear or branched heteroalkynyl groups, $C_3$-$C_{40}$ linear or branched cycloalkyl groups, $C_2$-$C_{40}$ heterocycloalkyl groups, $C_2$-$C_{40}$ linear or branched alkylcarboxylic groups, $C_2$-$C_{40}$ linear or branched alkylcarboxamide groups, $C_2$-$C_{40}$ linear or branched alkylimino groups, $C_1$-$C_{40}$ linear or branched alkylsulphonic groups, $C_1$-$C_{40}$ linear or branched alkyl nitrile groups, monocyclic aryl groups, substituted monocyclic aryl groups, polycyclic aryl groups, substituted polycyclic aryl groups, monocyclic heteroaryl groups, substituted monocyclic heteroaryl groups, polycyclic heteroaryl groups, substituted polycyclic heteroaryl groups, benzyl groups and substituted benzyl groups and combinations thereof as dimers, trimers and tetramers;

wherein for values of p=0, T is different from Ar', and for values of p from 1 to 5, T is different from Ar'';

with the exception of compounds of formula A:

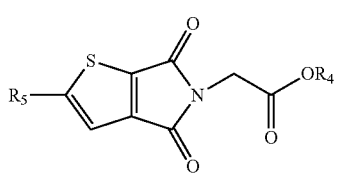

formula A wherein $R_4$ is selected in the group consisting of hydrogen and $C_1$-$C_4$ alkyls; and $R_5$ is selected in the group consisting of monocyclic aryl groups and substituted monocyclic aryl groups;

and with the exception of compounds of formula B:

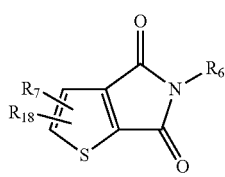

formula B wherein $R_6$ is selected in the group consisting of isopropyl, cyclopropyl and terbutyl groups, $R_7$ is selected in the group consisting of phenyl, 2-fluorphenyl, 3-fluorphenyl, 4-fluorphenyl, 2-chlorphenyl, 3-chlorphenyl, 4-chlorphenyl, 2-methylphenyl, 3-methylphenyl, 4-methylphenyl, 2-trifluoromethylphenyl, 3-trifluormethylphenyl, 4-trifluormethylphenyl, 2-methoxyphenyl, 3-methoxyphenyl, 4-methoxyphenyl, 2,4-dichlorphenyl, 2,4,6-trimethylphenyl, 2-thienyl, 3-thienyl, 2-pyridyl, 3-pyridyl, 4-pyridyl and $R_{18}$ is selected in the group consisting of hydrogen, fluorine, chlorine, methyl or methoxy groups.

In the present description and in the claims:

a "heteroalkyl group" is intended to include, for example, a halogenoalkyl group, a hydroxyalkyl group, a alkoxyalkyl group;

a "heteroalkenyl group" is intended to include, for example, a halogenoalkenyl group, a hydroxyalkenyl group, a alkoxyalkenyl group;

a "heteroalkynyl group" is intended to include, for example, a halogenoalkynyl group, a hydroxyalkynyl group, a alkoxyalkynyl group.

The value of p is preferably 0, 1 or 2.

The values of n and r are preferably comprised between 2 and 50, more preferably between 2 and 30, even more preferably between 2 and 10.

When p assumes the values of 0, then n is particularly preferably comprised between 2 and 50, more preferably between 2 and 30, even more preferably between 2 and 10.

Preferably, $R^3$ is hydrogen.

Preferably, Ar, Ar', Ar'', and T when aromatic, independently of each other, are selected in the group consisting of unsubstituted or substituted $C_6$-$C_{50}$ monocyclic aryl groups, $C_{10}$-$C_{50}$ polycyclic aryl groups, $C_{10}$-$C_{50}$ substituted polycyclic aryl groups, unsubstituted or substituted monocyclic $C_1$-$C_{50}$ heteroaryl groups, $C_6$-$C_{50}$ polycyclic heteroaryl groups, $C_6$-$C_{50}$ substituted polycyclic heteroaryl groups and combinations thereof as dimers, trimers and tetramers.

The preferred substituents of said monocyclic aryl groups, polycyclic aryl groups, monocyclic heteroaryl groups, polycyclic heteroaryl groups of Ar, Ar', Ar'' and T, are selected among halogens, alkyl, alkenyl, alkynyl or heteroalkyl groups. More preferably, said substituent groups are selected in the group consisting of linear or branched $C_1$-$C_{12}$ alkyl, linear or branched $C_2$-$C_{12}$ alkenyl, linear or branched $C_2$-$C_{12}$ alkynyl, $C_1$-$C_{12}$ perfluoroalkyl, $C_1$-$C_{12}$ oxyalkyl, $C_1$-$C_{12}$ aminoalkyl, $C_1$-$C_{12}$ thioalkyl, $C_1$-$C_{12}$ haloalkyl, $C_2$-$C_{12}$ carboxyalkyl groups, $C_1$-$C_{12}$ silicioalkyl groups.

Independently on the Ar, Ar' and Ar'' selection, the terminal group T is preferably selected in the group consisting of $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ fluoroalkyl groups, $C_1$-$C_{20}$ thioalkyl groups, $C_1$-$C_{20}$ silicioalkyl groups, $C_1$-$C_{20}$ alkylamino groups, $C_2$-$C_{20}$ alkylimino groups, phenyl groups, phenyl groups substituted with at least one $C_1$-$C_{10}$ alkyl group and/or with at least one $C_1$-$C_{10}$ heteroalkyl groups, thienyl groups, thienyl groups substituted with at least one $C_1$-$C_{10}$ allyl group and/or with at least one $C_1$-$C_{10}$ heteroalkyl groups, naphthalene, substituted naphthalene, antracene, substituted antracene, $C_4$-$C_{20}$ tricyclic heteroaryl groups.

More preferably, the terminal group T is selected in the group consisting of $C_1$-$C_{10}$ alkyl groups, $C_1$-$C_{10}$ perfluoroalkyl groups, $C_2$-$C_{10}$ alkenyl groups, phenyl groups, substituted phenyl groups, thienyl groups, substituted thienyl groups, pyridine, thiazole, benzodithiazole, thienothiophene, dithienothiophene, dibenzothiophene, fluorene, naphthalene, antracene, substituted naphthalene, substituted antracene, xantines and alkylimino groups.

According to an aspect of the present invention, the compounds of following formulas (Ia) and (IIa) are provided, which correspond to those of formulas (I) and (II), wherein p is equal to 0 and $R^3$ is hydrogen:

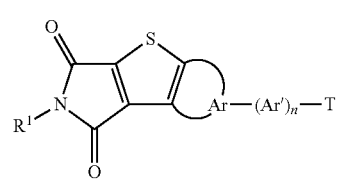

formula (Ia)

formula (IIa)

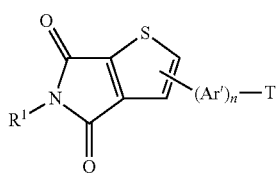

wherein R¹, Ar, Ar', T and n are as above defined.

In the present description and in the claims, the curved lines in formulas (I), (Ia), connecting the Ar moiety to the thienoimide unit, indicate that said Ar moiety forms a fused ring system with said thienoimide unit.

In addition, as usual in chemical drawing practice, in the present description and in the claims the bond lines crossing the thiophene double bond in formulas (II), (IIa), indicates that the $(Ar')_n$ moiety may be bound to any of the 2 or 3 position in the thiophene ring and is not fused thereto. Preferably, the $(Ar')_n$ moiety is bound to the 2 position of the thiophene ring.

In formulas (I) and (Ia), the $(Ar')_n$ and $(Ar'')_r$ moieties may be bound to any position of the Ar moiety that is fused to the thieno(bis)imide unit.

In formulas (Ia) and (IIa) the integer n is preferably comprised between 1 and 30, more preferably between 2 and 30, even more preferably between 2 and 10.

The compounds according to the invention wherein n is 2 are characterized by an advantageously high solubility in a number of solvents, for example dichloromethane, dimethyl sulfoxide, tetrahydrofuran, allowing for high level purification and easy solution processing.

Preferably, the Ar' is a unit selected among the following groups (a), (b), (c), (d), (e), (f), (g), (h), (i), (l), (m), (n), (o), (p), (q), (r):

(a)
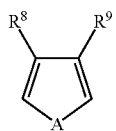

(b)
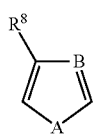

(c)
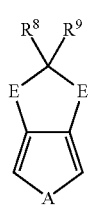

(d)
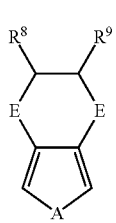

(e)
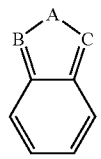

(f)
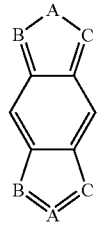

(g)
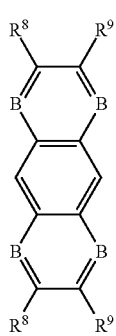

(h)
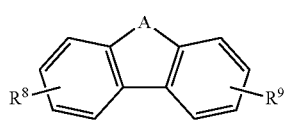

(i)
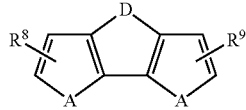

(l)
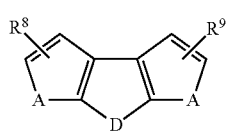

(m)
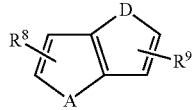

(n)
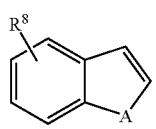

(o)
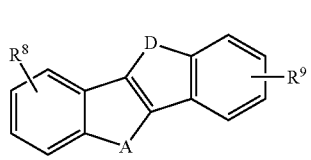

-continued

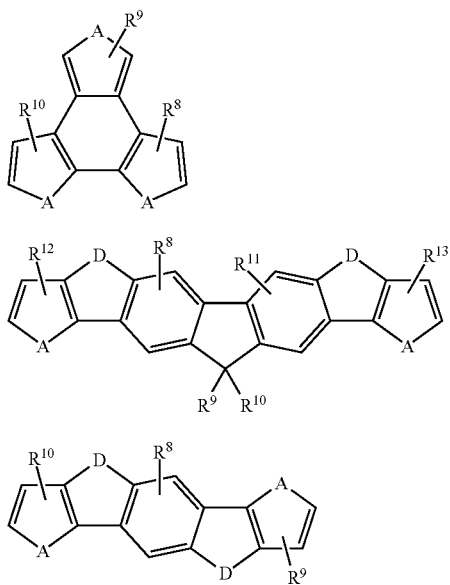

wherein A is selected in the group consisting of S, O Se, atoms and SO$_2$, SO$_2$, R$^{14}$—P=O, P—R$^{14}$, N—R$^{15}$, Si(R$^{15}$)$_2$ groups;

D is selected in the group consisting of C, S, O Se, atoms and SO, SO$_2$, R$^{14}$—P=O, PR$^{14}$, BR$^{14}$, N—R$^{15}$, Si(R$^{15}$)$_2$ groups;

B, C, independently of each other, are selected in the group consisting of C, N atoms;

E is selected in the group consisting of C(R$^{15}$)$_2$, S, O, and NR$^{15}$ group;

R$^8$, R$^9$, R$^{10}$, R$^{11}$, R$^{12}$ and R$^{13}$, independently of each other, are selected in the group consisting of hydrogen, halogens, C$_1$-C$_{20}$ linear or branched alkyl groups, C$_2$-C$_{20}$ linear or branched alkenyl groups, C$_2$-C$_{20}$ linear or branched alkynyl groups, C$_1$-C$_{20}$ linear or branched heteroalkyl groups, C$_2$-C$_{20}$ linear or branched heteroalkenyl groups, C$_2$-C$_{20}$ linear or branched heteroalkynyl groups, C$_3$-C$_{20}$ cycloalkyl groups, C$_2$-C$_{20}$ linear or branched heterocycloalkyl groups, C$_2$-C$_{20}$ linear or branched alkylcarboxylic groups, C$_2$-C$_{20}$ linear or branched alkylcarboxamide groups, C$_2$-C$_{20}$ linear or branched alkylimino groups, C$_1$-C$_{20}$ linear or branched alkylsulphonic groups, C$_1$-C$_{20}$ linear or branched alkyl nitrile groups, C$_5$-C$_{40}$ aryl groups, C$_1$-C$_{40}$ heteroaryl groups, C$_6$-C$_{40}$ alkylaryl groups;

R$^{14}$, R$^{15}$ independently of each other, are selected in the group consisting of hydrogen, C$_1$-C$_{20}$ linear or branched alkyl groups, C$_2$-C$_{20}$ linear or branched alkenyl groups, C$_2$-C$_{20}$ linear or branched alkynyl groups, C$_1$-C$_{20}$ linear or branched heteroalkyl groups, C$_2$-C$_{20}$ linear or branched heteroalkenyl groups, C$_2$-C$_{20}$ linear or branched heteroalkynyl groups, C$_3$-C$_{20}$ linear or branched cycloalkyl groups, C$_2$-C$_{20}$ linear or branched heterocycloalkyl groups, C$_2$-C$_{20}$ linear or branched alkylcarboxylic groups, C$_2$-C$_{20}$ linear or branched alkylcarboxamide groups, C$_2$-C$_{20}$ linear or branched alkylimino groups, C$_1$-C$_{20}$ linear or branched alkylsulphonic groups, C$_1$-C$_{20}$ linear or branched alkyl nitrile groups, C$_5$-C$_{40}$ aryl groups, C$_1$-C$_{40}$ heteroaryl groups, C$_6$-C$_{40}$ alkylaryl groups.

In formulas (h), (i), (l), (m), (n), (o), (p), (q), (r), it is meant that the substituent group may be bound to any carbon position of any ring forming the delocalized system.

Examples of the above described groups of formula (a)-(r) are for example the following:

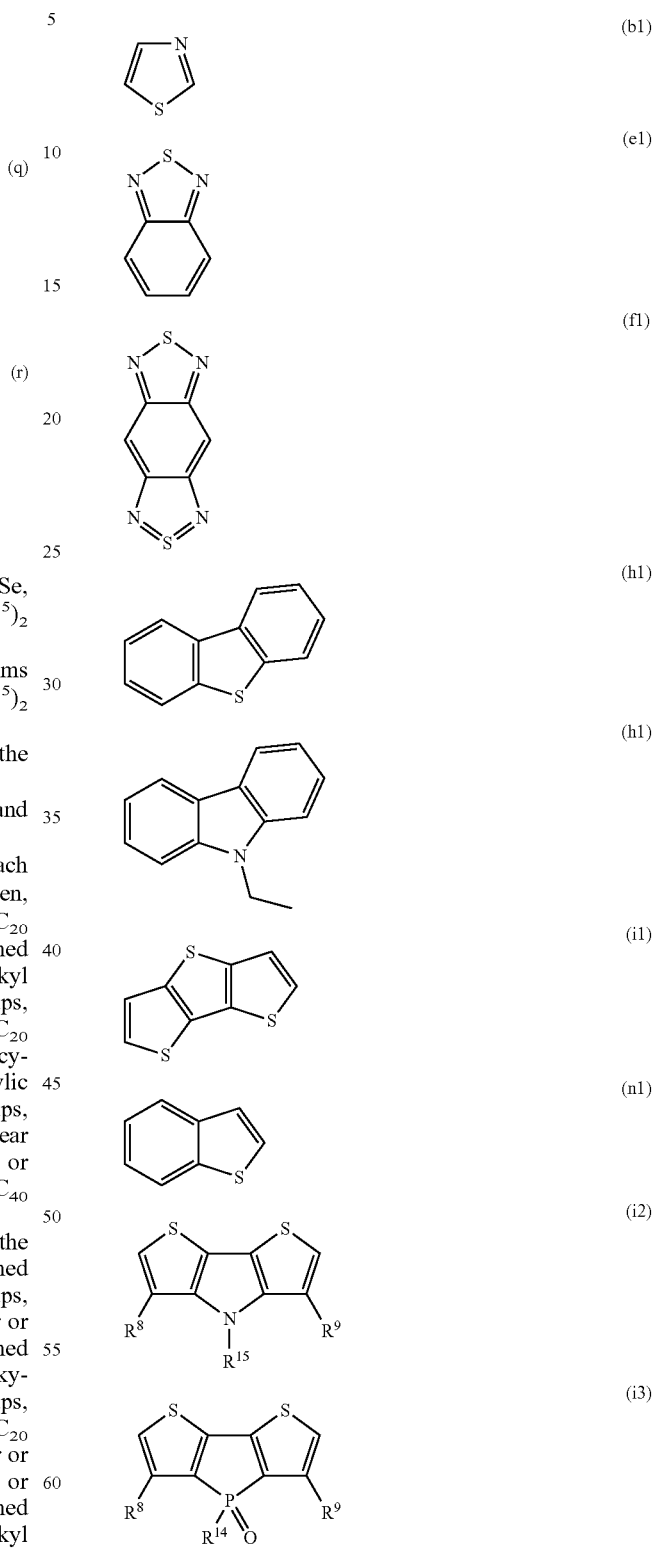

In other preferred embodiments of the present invention, the Ar' moiety may be a dimer comprising a thiophene, thiazole, furane, benzothiazole, thienothiophene or phenyl unit that is linked to another aryl unit, such as the above represented (a)-(r) groups, like in the following formulas (s) and (t):

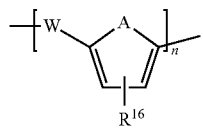
(s)

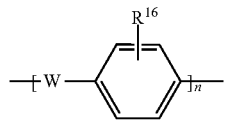
(t)

wherein W is a moiety selected in the group consisting of the above indicated groups (a) to (r), and $R^{16}$ is a moiety selected in the same group as $R^8$—$R^{13}$.

More preferably, the Ar' group may be a dimer comprising a thiophene unit that is α-linked to a polycyclic or oligomeric unit such as in the following $(Ar')_n$ moieties of formula (u), (v), (w), (x) and (y):

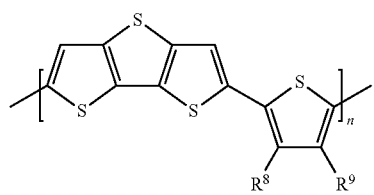
(u)

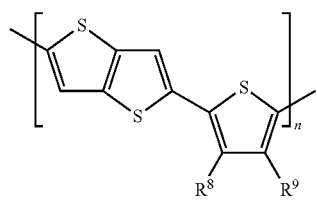
(v)

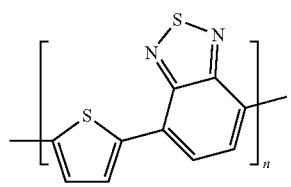
(w)

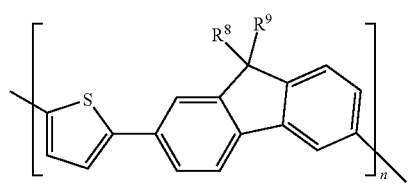
(x)

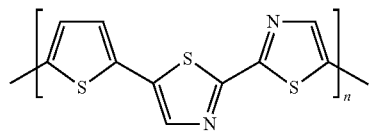
(y)

wherein $R^8$, $R^9$ and n have the above described meanings.

In an embodiment of the invention, Ar' is a thiophene unit or substituted thiophene unit, wherein the $(Ar')_n$ moiety is a linear chain of a-linked thiophene units or substituted thiophene units.

The Ar moiety fused to the thienoimide unit of the compounds of formulas (I) and (Ia) according to the present invention may be advantageously formed of one, two or three aromatic rings.

Preferably, in formulas (I), (Ia), Ar is selected in the group consisting of the following rings (α), (β), (γ), (δ), (∈), (ζ), (η), (θ), (ι):

(α)

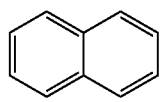
(β)

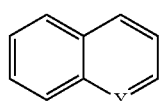
(γ)

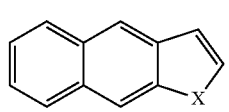
(δ)

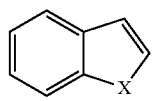
(ε)

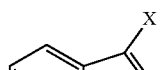
(ζ)

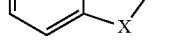
(η)

(θ)

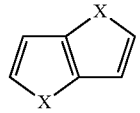
(ι)

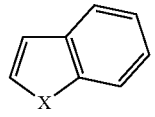

wherein X is selected in the group consisting of S, SO, $SO_2$, O, Si, Sc, $NR^{17}$, Y is selected in the group consisting of C and N;

$R^{17}$ is selected in the group consisting of hydrogen, $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ linear or branched heteroalkyl groups, $C_2$-$C_{20}$ linear or branched heteroalkenyl groups, $C_2$-$C_{20}$ linear or branched heteroalkynyl groups, $C_3$-$C_{20}$ linear or branched cycloalkyl groups, $C_2$-$C_{20}$ heterocycloalkyl groups, $C_2$-$C_{20}$ linear or branched alkylcarboxylic groups, $C_2$-$C_{20}$ linear or branched alkylcarboxamide groups, $C_2$-$C_{20}$ linear or branched alkylimino groups, $C_1$-$C_{20}$ linear or branched alkylsulphonic groups, $C_1$-$C_{20}$ linear or branched alkyl nitrile groups, $C_5$-$C_{40}$ aryl groups, $C_1$-$C_{40}$ heteroaryl groups, $C_6$-$C_{40}$ alkylaryl groups Specific examples of compounds of formula (IIa) according to the present invention are for example the following compounds 6 and 8-18:

compound 6

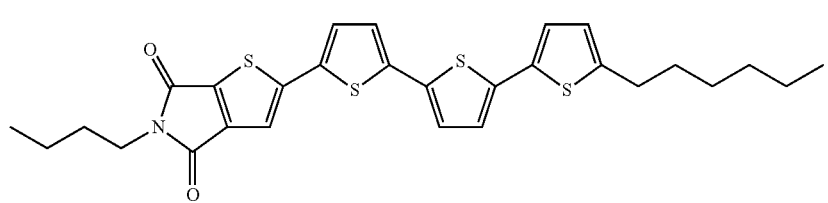 [SMILES: CCCCCCc1ccc(-c2ccc(-c3ccc(-c4cc5c(s4)C(=O)N(CCCC)C5=O)s3)s2)s1]

compound 8

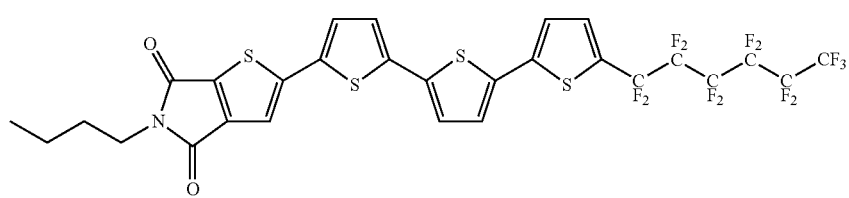

compound 9

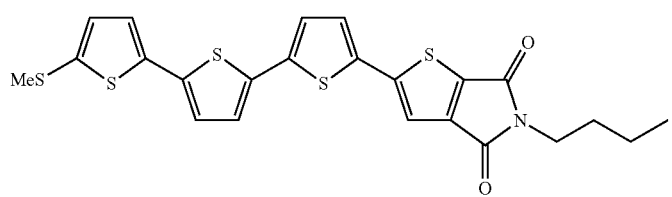

compound 10

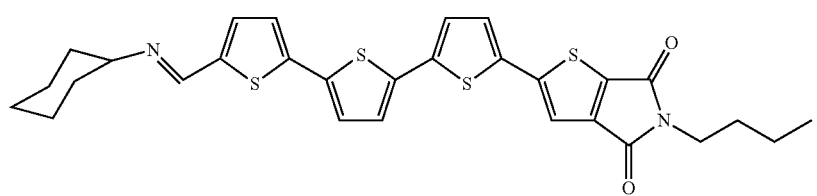

compound 11

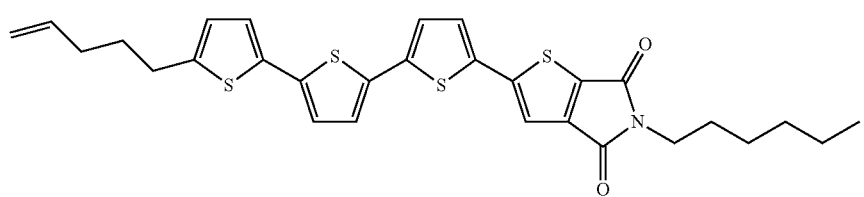

compound 12

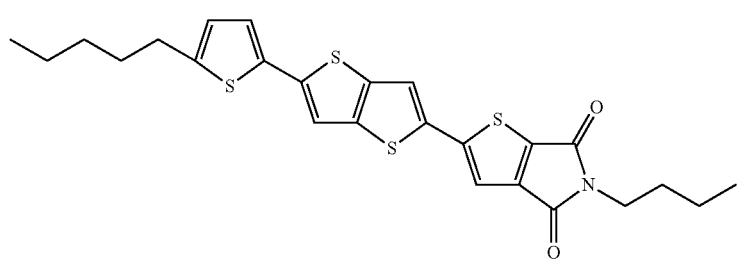

compound 13

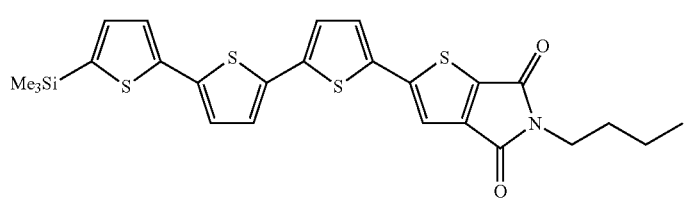

-continued compound 14
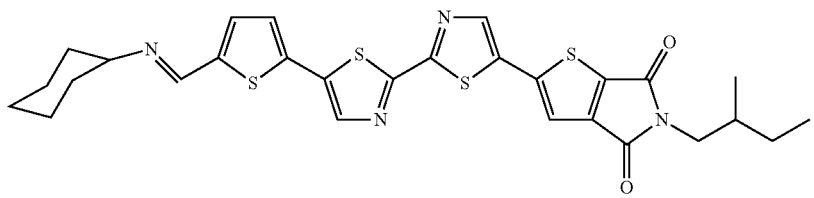

compound 15
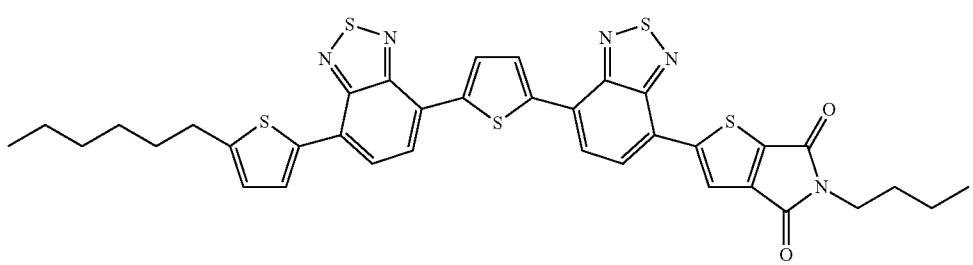

compound 16
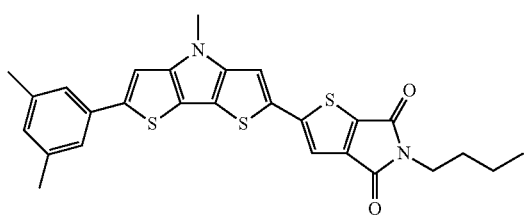

compound 17
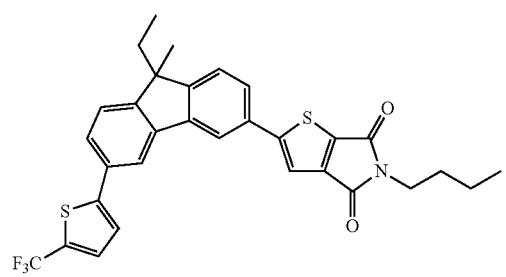

compound 18
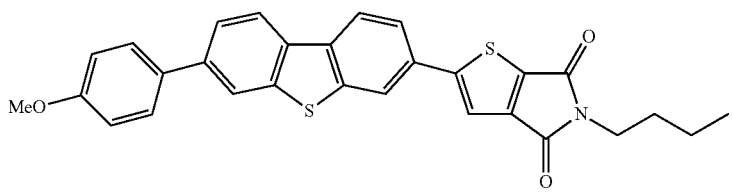

Without wishing to limit the present invention to any theory, it is believed that the thiopheneimide moiety due to its strong electrowithdrawing effect can increase the overall electron affinity of π-conjugated materials promoting the electron charge transport capability. On the other hand, the opposite terminal groups may be exploited to tune the dipole moment, the HOMO LUMO energy levels and orbital distribution and the packing modality, this ultimately influencing the functional properties of the resulting materials. Compounds 6 and 8 are particularly advantageous, being additionally provided with good electroluminescence, as shown in the following examples.

Among the main advantages of such compounds with respect to other classes of n-type materials are to be mentioned the easy accessibility and structural versatility.

The thienoimide moiety can be coupled to selected π-conjugated cores by cross-couplings under conventional or microwave-assisted heating as described below or by direct arylation reaction.

The easy accessibility of the compounds according to the invention also allows an easy modification of the oligomer size, and degree and type of molecular functionalization, which in turn permits application fine property-specific design toward the targeted applications.

The compounds according to the present invention can be obtained with electronic level of purity by chromatography, crystallization and sublimation, with unambiguous molecular structure determination through classic analytical methods.

Contrarily to the thiophene-3,4-imide based polymers, bithiophene-imide polymers and perylene tetrarboxylic diimide systems according to the prior art, this class of materials can be prepared with high reproducibility from batch to batch, which is crucial to achieve devices with reproducible responses.

According to still another aspect of the invention, it is provided a process for the production of a compound according to the invention, wherein the process comprises reiterative halogenation of aromatic compounds and cross-coupling reactions.

The processes according to the present invention are preferably catalyzed by palladium.

The compounds according to the invention of formulas (I), (II) may be obtained starting from an aromatic dihalide, such as in the following Schemes 1 and 2:

Scheme 1

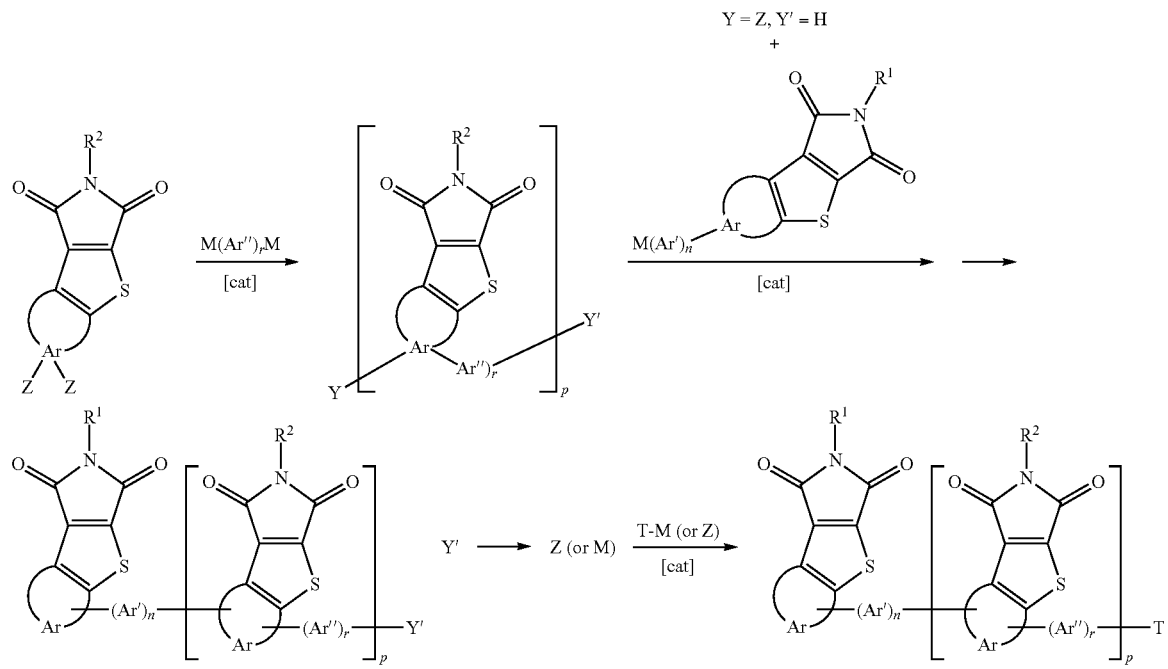

Scheme 2

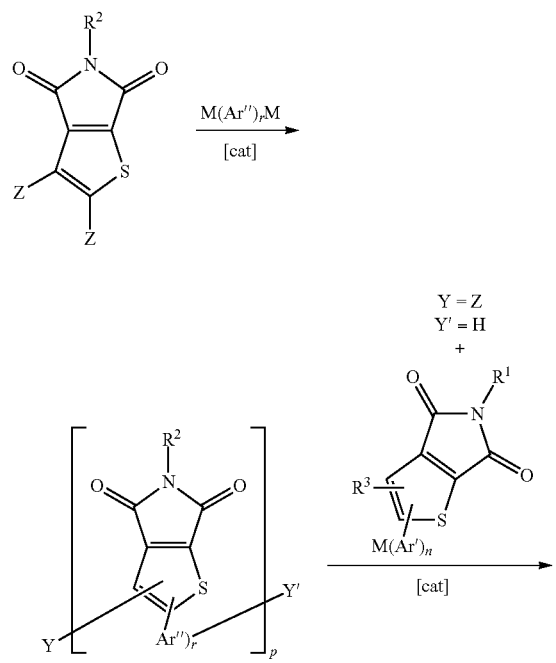

wherein Z is selected among halogen atoms, such as Br, I; M is an organometal compound such as B(OR')$_2$ and SnR"$_3$ wherein R' is an hydrogen or an alkyl moiety and R" is an alkyl moieties; and [cat] is a palladium based catalyst. Alternatively, Z can be hydrogen and can undergo direct CH arylation reaction under Pd catalysis.

Scheme 1a shows possible synthetic approaches for the preparation of the starting materials of the process of scheme 1, wherein Z is halogen and NZS means halogenated succinimide. Depending on the type of the fused heterocycle, pathway a or b should be selected.

Scheme 1a a)

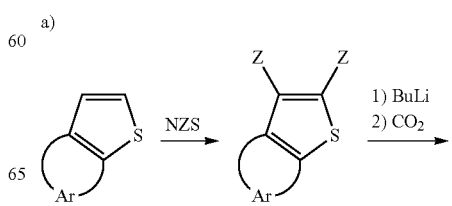

-continued

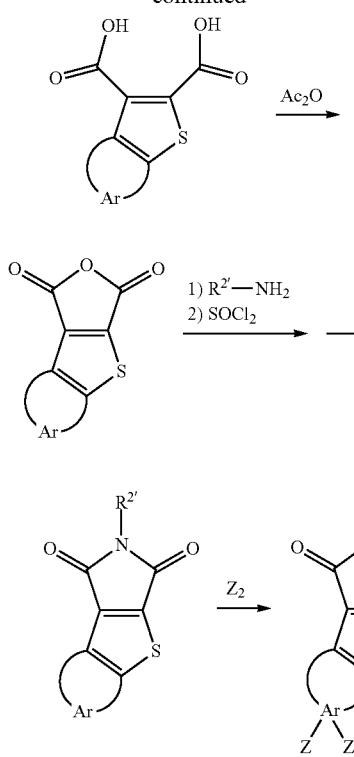

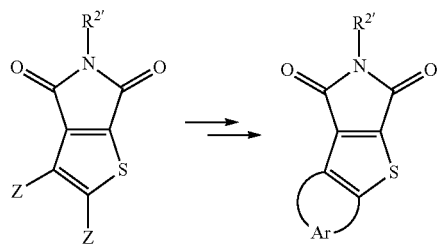

b)

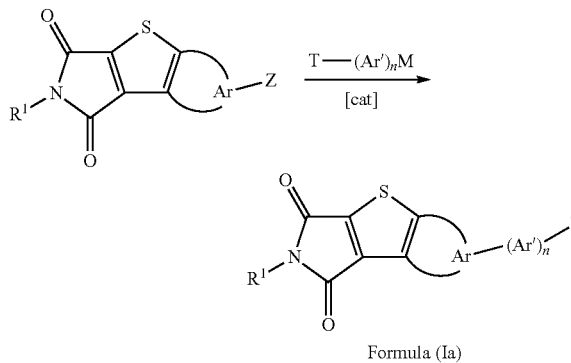

The compounds of formulas (Ia), (IIa), may be obtained according to the present invention by means of processes as outlined in the following Schemes 3 and 4:

Scheme 3

Scheme 4 wherein Z is selected among halogen atoms, such as Br, I; M is an organometal compound such as $B(OR')_2$ and $SnR''_3$ wherein R' is selected in the group consisting of hydrogen and alkyl moieties, and R'' is selected in the group consisting of alkyl moieties; and [cat] is a palladium based catalyst. For example, tetrakis triphenylphosphine palladium (0) can be used as catalyst.

In another aspect thereof, the present invention relates to a semiconductor material, comprising at least one compound according to formulas (I) and/or (II). Preferably, said semiconductor material comprises at least one compound according to formulas (Ia) and/or (IIa).

In an embodiment thereof, said semiconductor material comprises one or more of compounds 6 and 8 to 18, preferably compounds 6 and/or 8.

According to another aspect, the invention relates to an electronic device comprising a semiconductor layer in contact with a number of electrodes, wherein the semiconductor layer includes at least one compound according to formulas (I) and/or (II). Preferably, said semiconductor layer comprises at least one compound according to formulas (Ia) and/or (IIa). More preferably, said semiconductor layer, comprises at least one compound selected among compounds 6 and 8 to 18.

In an embodiment thereof, said semiconductor layer comprises compound 6 and/or compound 8.

Preferably, said electronic device comprising a semiconductor layer including the compounds according to the present invention is selected among optical devices, electrooptical devices, field effect transistors, integrated circuit, thin film transistors, organic light-emitting devices, and organic solar cells.

Particularly, thin films of the thienoimide based materials according to the invention can be used as active layers in OFETs and OLET devices as demonstrated in the following examples. They can be used as electron- or hole-transporting layer or ambipolar semiconductor in single layer OFET, as multifunctional electron- and hole-transporting and light emitting layer in single layer OLET, and as hole or electron transporting layer in multi-layer OLET.

Finally, applications of compounds and materials according to the present invention in organic photovoltaics can be envisaged.

In the following examples, all $^1H$, $^{13}C$, and $^{19}F$ NMR spectra were recorded at room temperature on a Varian Mercury 400 spectrometer operating at 400 MHz ($^1H$) and 100.6 MHz ($^{13}C$). Chemical shifts were calibrated using the internal $CDCl_3$, acetone-$d_6$ or $CD_2Cl_2$ resonance which were referenced to TMS. In the $^{19}$F NMR spectra 0.5% fluorobenzene was added as an internal standard. The fluorobenzene was referenced to CFCl$_3$.

Mass spectra were collected on an ion trap Finningan Mat GCQ spectrometer operating in electron impact (EI) ionization mode. Each sample was introduced to the ion source region of the GCQ via a direct exposure probe (DEP).

Melting points were determined on a 'hot-stage' apparatus where the melting process was observed with the aid of a microscope.

UV-Vis spectra were recorded using a Perkin Elmer Lambda 20 spectrometer. Photoluminescence spectra were obtained with a Perkin Elmer LS50B spectrofluorometer using an excitation wavelength corresponding to the maximum absorption lambda.

Differential Scanning calorimetry (DSC) analysis were performed by using a Thass DSC-XP-10 instrument under atmospheric conditions.

5-tributylstannyl-2,2'-bithiophene, 2-hexyl-5-tributylstannyl-thiophene 2-perfluorohexyl-5-tributhylstannyl-thiophene were purchased from Sigma-Aldrich Co. Thiophene-2,3-dicarboxylic anhydride, was prepared according to already reported procedures.

Cyclic Voltammetry measurements have been performed at room temperature, after Ar purging, with an AMEL 5000 electrochemical system in CH$_2$Cl$_2$ (Carlo Erba RPE, distilled over anhidrous P$_2$O$_5$ and stored under Ar pressure) and 0.1 M (C$_4$H$_9$)$_4$NClO$_4$ (Fluka, puriss. crystallized from methanol and vacuum dried). The electrochemical cell was in three compartment shape, with Pt semi sphere electrode (diameter 2 mm), Pt wire counter electrode and aqueous KCl Saturated Calomel Electrode (SCE=0.47 V vs. ferrocene/ferricinium). The concentration of the compounds were 1.1 mmol L$^{-1}$.

AFM on vacuum sublimed films was performed by using a NT-MDT Solver Pro AFM atomic force microscope in tapping mode.

EXAMPLE 1

Synthesis of 2-(5"-hexyl-2,2':5',2"-terthiophene-5-yl)-5-butyl-5H-thieno[3,2-c]pyrrole-4,6-dione, Compound 6:

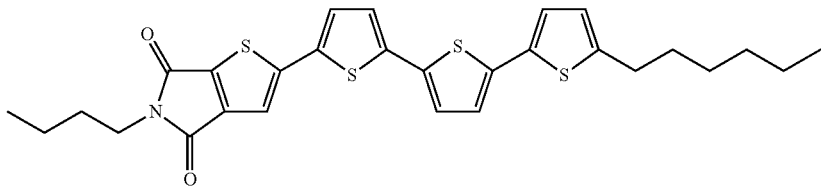

The synthesis was performed according to the below reported scheme.

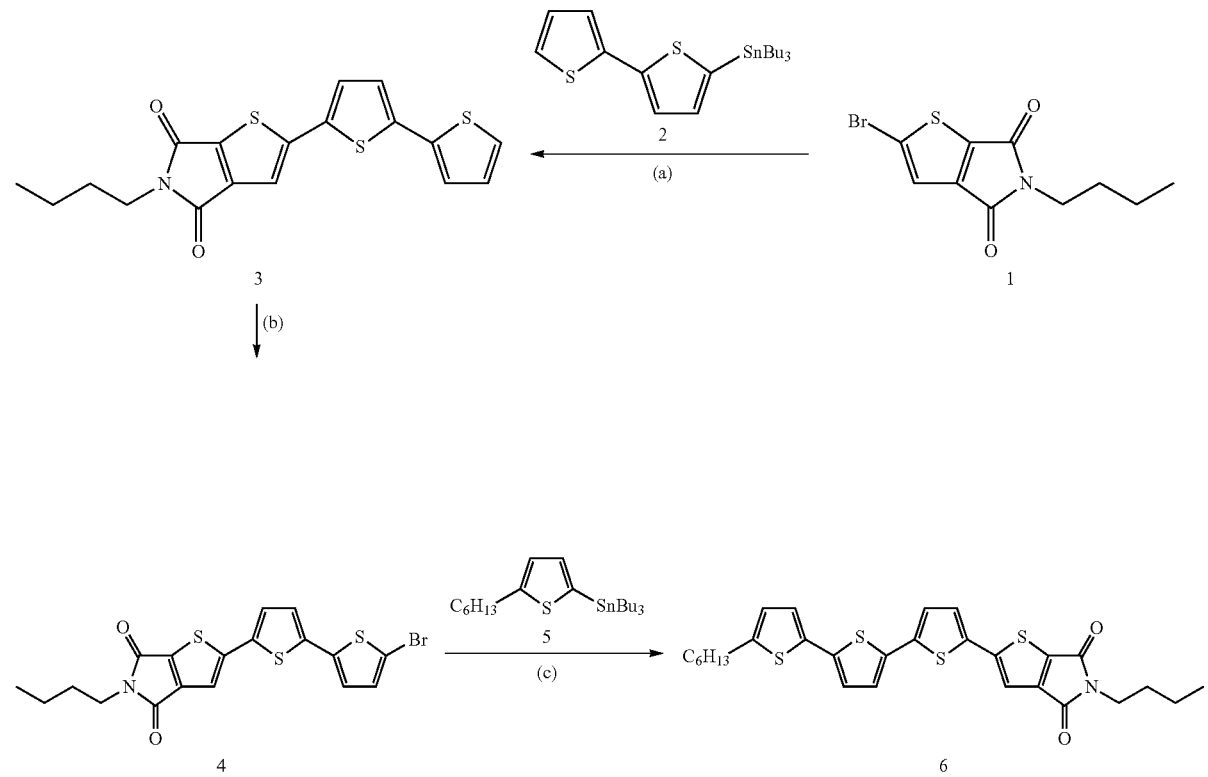

Step (a): Synthesis of 2-([2,2'-bithiophen]-5-yl)-5-butyl-4H-thieno[2,3-c]pyrrole-4,6(5H)-dione, 3

To a refluxing toluene solution (8 ml) of compound 1 (82 mg, 0.28 mmol) and in situ-prepared Pd(AsPh$_3$)$_4$ (8 mol %, 11 mg of Pd$_2$dba$_3$ and 27 mg of AsPh$_3$) under N$_2$ atmosphere, 5-(tributylstannyl)-2,2'-bithiophene, 2 (135 mg, 0.3 mmol) in toluene (0.5 ml), was added dropwise. The solution was refluxed for 6 h, then the solvent was removed under vacuum and the crude product purified by flash chromatography on silica gel by using a solution of pet. eth./DCM/AcOE=90:5:5 as eluent. Compound 3 was isolated as a orange powder (83 mg, yield 79%) and used for the following step without further purification. MS (70 eV, EI): m/z 373 (M.$^{+1}$). $^1$H NMR (CDCl$_3$, TMS/ppm) δ: 7.29 (s, 1 H), 7.28 (dd, $^3$J=5.2 Hz, $^4$J=1.2 1H), 7.23 (m, 2H), 7.12 (d, $^3$J=3.6 Hz 1H), 7.05 (dd, $^3$J=5.2 Hz, $^3$J=4.8 1H), 3.60 (t, 2H), 1.63 (m, 2H), 1.36 (m, 2H), 0.95 (t, 3H). $^{13}$C NMR (CDCl$_3$, TMS/ppm): 163.9, 162.8, 149.9, 145.2, 139.3, 137.1, 136.1, 133.6, 128.1, 126.7, 125.5, 124.7, 124.5, 116.3, 38.3, 30.8, 20.0, 13.6.

Step (b): Synthesis of 2-(5'-bromo-[2,2'-bithiophen]-5-yl)-5-butyl-4H-thieno [2,3-c]pyrrole-4,6 (5H)-dione, 4

Compound 3 (90 mg, 0.24 mmol) obtained as in step (a) was dissolved in 8 ml of a 1:1 mixture of dichloromethane and acetic acid solution. NBS (50 mg, 0.28 mmol) was added and the reaction mixture was stirred at room temperature over night in darkness. The yellow solution so obtained was then diluted with 10 ml of water, extracted with dichloromethane, washed with 10% NaHCO$_3$, and water. The organic phase was dried over anhydrous sodium sulfate and evaporated and the crude product purified by flash chromatography on silica gel by using pet. eth./AcOEt 94:6 to 80:20 as eluent. Compound 4 was isolated as a orange powder (97% yield). M.p. 153° C., MS (70 eV, EI): m/z 451, 453 (M.$^{+1}$). $^1$H NMR (CDCl$_3$, TMS/ppm) δ: 7.29 (s, 1H), 7.21 (d, $^3$J=4.0 Hz, 1H), 7.05 (d, $^3$J=3.6 Hz, 1H), 7.00 (d, $^3$J=4.0 Hz, 1H), 6.96 (d, $^3$J=4.0 Hz, 1H), 3.60 (t, 2H), 1.62 (m, 2H), 1.36 (m, 2H), 0.95 (t, 3H). $^{13}$C NMR (CDCl$_3$, TMS/ppm) 163.9, 162.7, 149.5, 145.2, 138.1, 137.6, 137.4, 134.0, 130.9, 126.7, 124.8, 124.7, 116.7, 112.3, 38.3, 30.8, 20.0, 13.6.

Step (c): Synthesis of 2-(5''-hexyl-2,2':5',2''-terthiophene-5-yl)-5-butyl-5H-thieno[3,2-c]pyrrole-4,6-dione: 6

To a refluxing toluene solution (12 ml) of Pd(AsPh$_3$)$_4$ (8 mol %, prepared in situ) and compound 4 (0.22 mmol), obtained as in step (b), under N$_2$ atmosphere, compound 5 (0.26 mmol) diluted in 3 ml of toluene was added dropwise. The solution was refluxed for 8 h, then the solvent was removed under vacuum. The crude was purified by flash chromatography on silica gel, eluent: pet. eth./Ethyl Acetate 95:5 to 0:100, followed by crystallization.

Compound 6 was obtained as an orange powder (68% yield). M.p. 178° (K→LC), 260°; MS (70 eV, EI): m/z 539 (M.$^{+1}$). $^1$H NMR (CDCl$_3$, TMS/ppm): 7.28 (s, 1H), 7.22 (d, $^3$J=3.6 Hz, 1H), 7.10 (d, $^3$J=3.6 Hz 1H), 7.09 (d, $^3$J=4.0 Hz, 1H), 7.01 (d, $^3$J=4.0 Hz, 1H), 7.00 (d, $^3$J=3.6 Hz, 1H), 7.69 (d, $^3$J=3.6 Hz, 1H), 3.60 (t, 2H), 2.80 (t, 2H), 1.66 (m, 4H), 1.35 (m, 8H), 0.92 (m, 6H). $^{13}$C NMR (CDCl$_3$, TMS/ppm): 163.9, 162.8, 149.9, 146.2, 145.3, 139.2, 138.2, 137.0, 134.0, 133.3, 126.7, 125.2, 124.9, 124.2, 123.8, 123.7, 116.2, 38.3, 31.5, 30.9, 30.2, 28.7, 22.6, 20.0, 14.1, 13.6. Anal. Calcd for C$_{28}$H$_{29}$NO$_2$S$_4$ (539.80): C, 62.30; H, 5.42. Found: C, 62.24; H, 5.49.

In the DSC thermograms of compound 6 (second run, 10° C./min) in air, compound 6 shows the melting transition at about 157° C., followed by a transition LC1→LC 2 at 179° C. Finally, isotropization occurred at 246° C.

Figure 1:
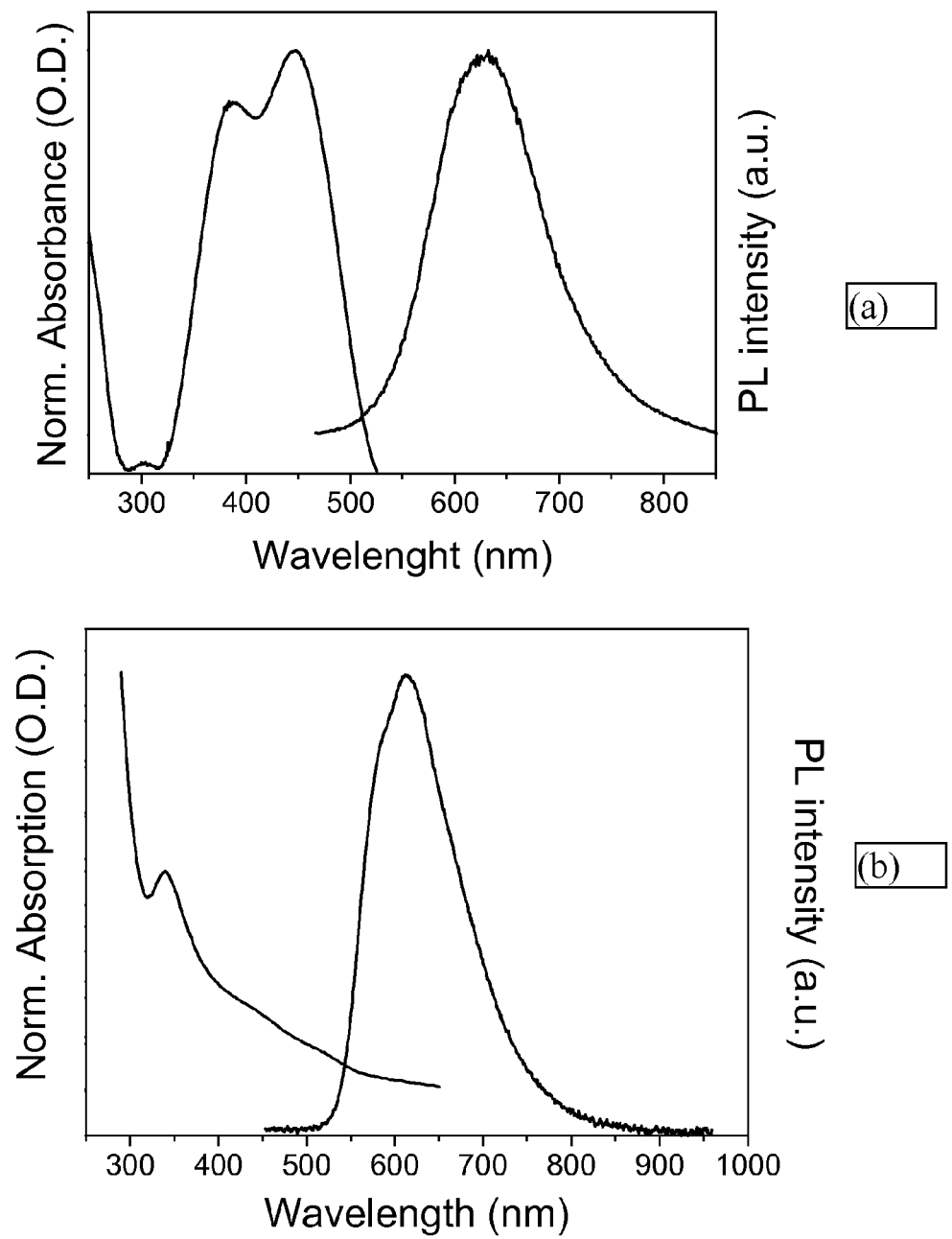

Optical spectroscopy of compound 6 was performed. FIG. 1(a) shows the absorption and emission spectra of compound 6 in CH$_2$Cl$_2$ solution and FIG. 1(b) the absorption and emission spectra of compound 6 as a vacuum sublimed film of 30 nm thickness.

Figure 2:
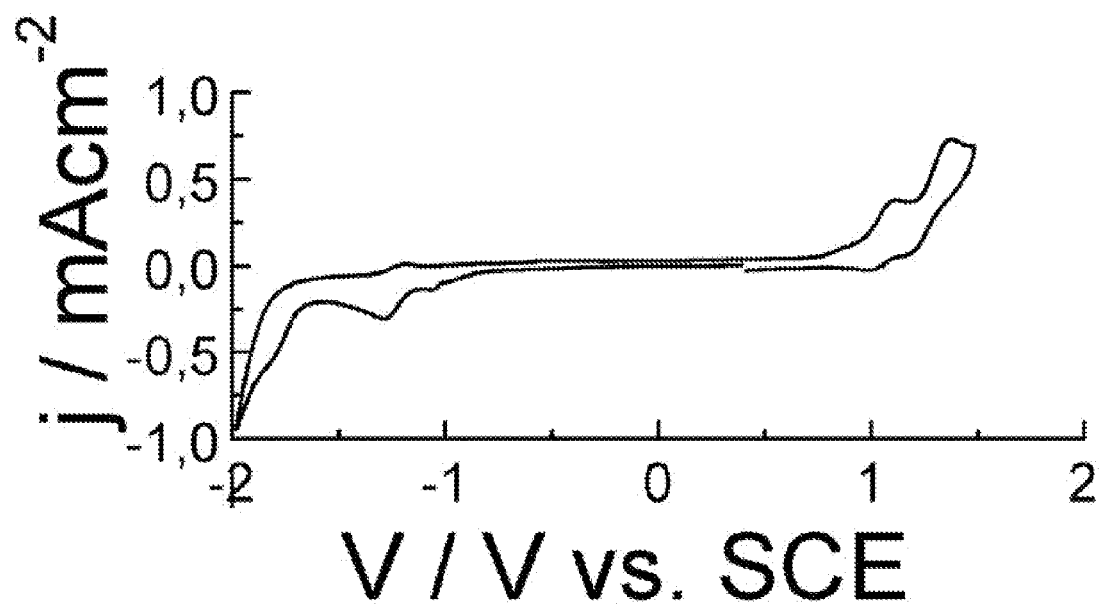
FIG. 2 shows a cyclic voltammetry of a preferred compound 6 according to the present invention.

CVs of compound 6 (1.1 mmol l$^{-1}$) at 100 mV/s in CH$_2$Cl$_2$, 0.1 mol l$^{-1}$ (C$_4$H$_9$)$_4$NClO$_4$ is shown in FIG. 2. The voltammogram of compound 6 shows two oxidation waves at E°$_{ox1}$=1.05 V and E°$_{ox2}$=1.28 V. On the other hand, it shows a quasi-reversible reduction wave at E°$_{red1}$=−1.24 V, and an irreversible reduction wave at E$^{1/2}_{red2}$=−1.75 V due to the oligothiophene moiety.

Table 1 reports a summary of the optoelectronic properties measured for compound 6.

| Comp. | λ$_{abs}$ nm$^a$ (theor) | λ$_{PL}$ nm$^a$ | E$_g^{opt}$ eV | λ$_{abs}$ Film$^b$ (nm) | λ$_{PL}$ film$^b$ (nm) | HOMO eV$^c$ (theor)$^c$ | LUMO eV$^c$ (theor) | E$_g^{ec}$ eV |
|---|---|---|---|---|---|---|---|---|
| compound 6 | 447 (450) | 631 | 2.77 | 340 | 584/611 | −5.73 (−5.14) | −3.42 (−2.31) | 2.31 |

$^a$in CH$_2$Cl$_2$,
$^b$30 nm thick film,
$^c$E$_{HOMO}$ = e (4.68 − E°$_{ox}$); E$_{LUMO}$ = e (4.68 − E°$_{red}$)

X-ray diffraction analysis was carried out by means of a PANalytical X'Pert diffractometer equipped with a copper anode (λ$_{mean}$=0.15418 nm) and a fast X'Celerator detector. Step 0.05° (2theta scale), counting time 400 sec. Films grown on Si/SiO2 substrates or on OFET device (counting time 1200 sec) were directly investigated.

Figure 3:
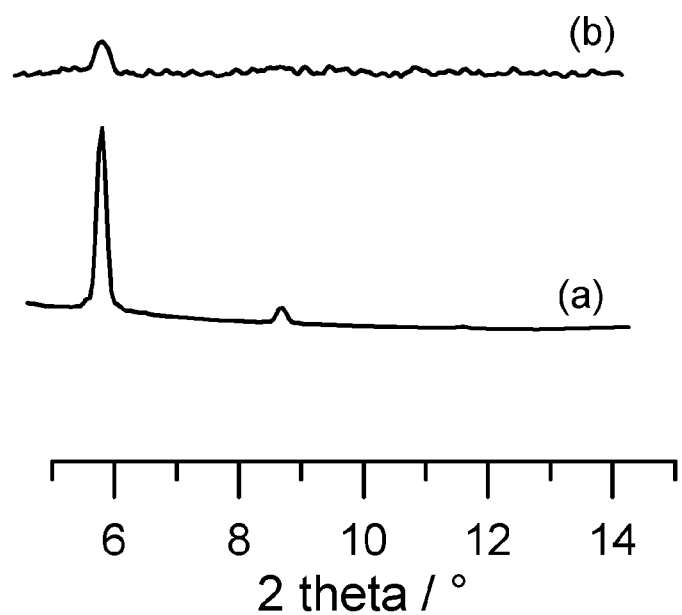
FIG. 3(a) shows a X-ray diffraction analysis of a compound 6 according to the present invention on a SiO2 substrate.
FIG. 3(b) shows a X-ray diffraction analysis of a compound 6 according to the present invention on a OFET device.

FIG. 3 shows the results of a X-ray diffraction analysis of compound 6. FIG. 4(a) shows an XRD pattern obtained from a 30 nm film of compound 6 on SiO$_2$ substrate (counting time 400 sec/step) and FIG. 4(b) shows an XRD pattern obtained from film grown on a PMMA substrate of an OFET device (counting time 1200 sec/step).

Figure 4:
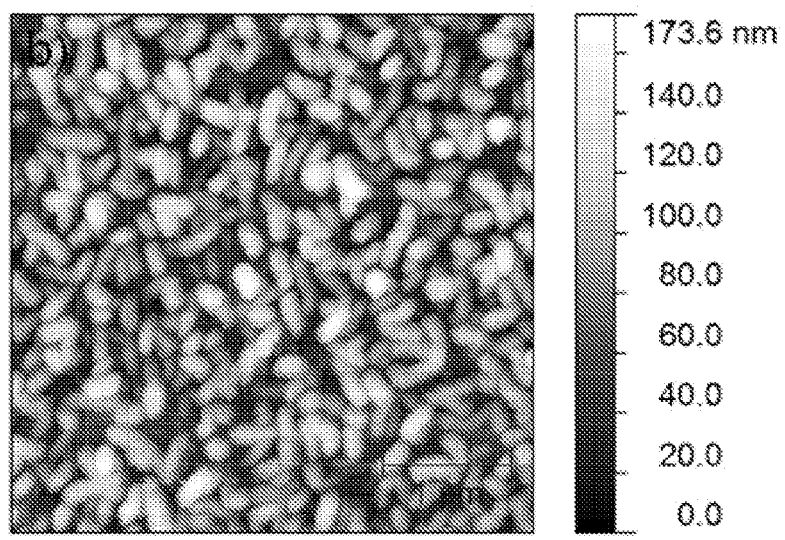
FIG. 4 shows an Atomic Force image of a 30 nm thick film of compound 6 according to the present invention, grown on PMMA.

FIG. 4 is the atomic force microscope image showing the morphology of a thin film (30 nm) of compound 6 grown on a 450 nm thick layer of PMMA which is deposited on a ITO layer.

EXAMPLE 2

Fabrication and Optoelectronic Measurements of Field Effect Transistor (OFET)

Organic thin film transistors were fabricated in bottom gate-top contact geometry. An ITO substrate was cleaned be means of two sonication cycles, first in acetone and then 2-isopropanol, for 10 minutes each. Then a 450 nm thick dielectric layer of PMMA was grown by spin-coating on top of the clean ITO substrate. The relative electric permittivity ∈ was 3.6 at 100 Hz. The PMMA layer was then thermally annealed in a glove box at 120° C. (i.e., around 10° C. above the glass transition temperature for PMMA) for 15 hours under inert atmosphere. (CPMMA=7.08 nF/cm$^2$).

Then, an organic thin film layer consisting of compound 6 was grown on the top of said dielectric layer by vacuum sublimation in a vacuum chamber, with a deposition rate of 0.1 Å/s, at a base pressure of $10^{-6}$ mbar. The substrate temperature during the film deposition was kept at room temperature (RT).

Then, gold drain and source electrodes were made on top of the organic thin film by evaporation through a shadow mask. The thickness of said gold drain and source electrodes was 50 nm, while the channel length (L) and the channel width (W) were 70 μm and 12 mm, respectively.

The electrical characteristics of such a transistor were then measured. All opto-electronic measurements were carried out in an MBraun nitrogen glove box using a standard SUSS Probe Station equipped with a Hamamatsu photodiode for light detection.

The mobility values in saturation were calculated from the locus curves using the standard equations:

$$\mu = L/(W*C)A^2 \quad [eq. 1]$$

wherein A is the angular coefficient of the line fitting the square root of the drain current vs the applied voltage, L is the channel length, W the channel width and C is the transistor dielectric capacitance.

FIG. 5(a) shows the output curve of such transistor comprising an organic layer consisting of compound 6. FIG. 5(b) shows the transfer curve of such transistor comprising an organic layer consisting of compound 6.

EXAMPLE 3

Fabrication and Optoelectronic Measurements of Organic Light Emitting Transistor (OLET)

An organic light emitting transistor was fabricated, having the configuration of the transistor of example 2, therefore the same fabrication procedure was followed.

The electrical characteristics of such a transistor were then measured with the same methods as for example 2, and transfer curves were obtained.

Table 2 reports a summary of the electrical parameters measured for a 30 nm layer formed of compound 6 in an OLET device.

TABLE 2

| Comp. | $\mu_h$ (cm$^2$V$^{-1}$S$^{-1}$) | $V_T^P$/V | $I_{on}/I_{off}$ | $\mu_e$ (cm$^2$V$^{-1}$S$^{-1}$) | $V_T^N$/V | OLET emission power (nW) |
|---|---|---|---|---|---|---|
| compound 6 | $3.1 \times 10^{-3}$ | −17.5 | $10^4$ | $2.8 \times 10^{-5}$ | 10.9 | 8 |

EXAMPLE 4

Synthesis of 2-(5″-(perfluorohexyl)-2,2′:5′,2″-terthiophene-5-yl)-5-butyl-5H-thieno[3,2-c]pyrrole-4,6-dione, Compound 8

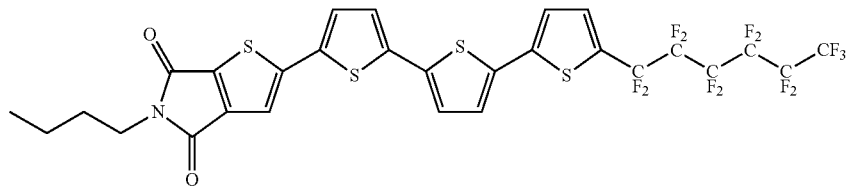 [SMILES: CCCCN1C(=O)c2cc(-c3ccc(-c4ccc(-c5ccc(C(F)(F)C(F)(F)C(F)(F)C(F)(F)C(F)(F)C(F)(F)F)s5)s4)s3)sc2C1=O]

The synthesis was performed according to the below reported scheme:

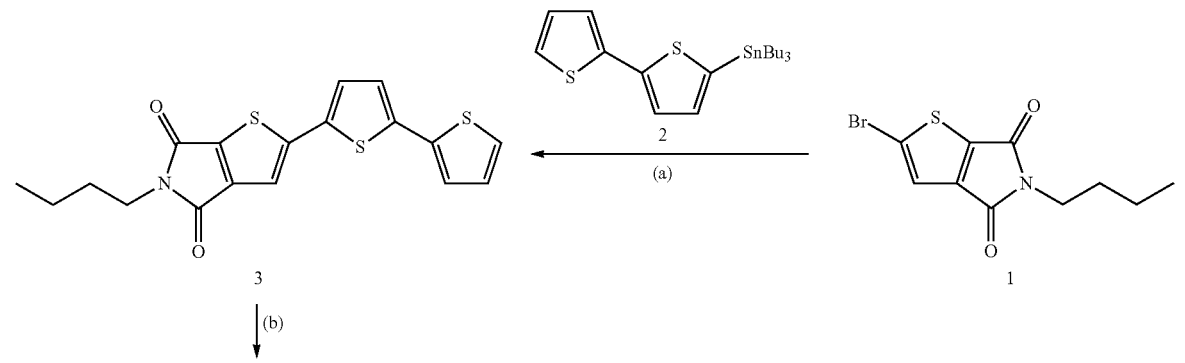

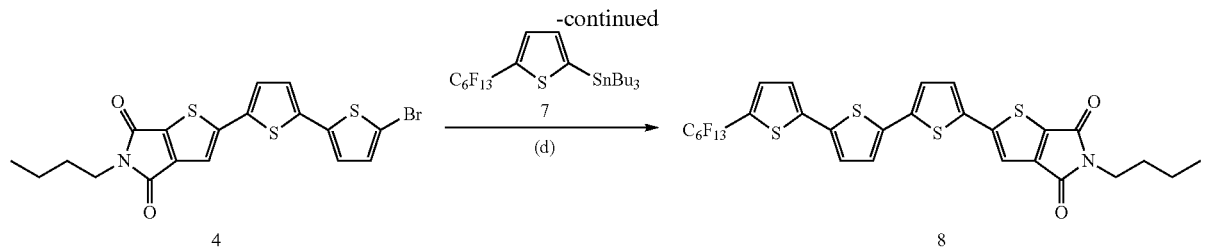

Compounds 3 and 4 were obtained as described in Example 1, steps (a) and (b).

Step (d): Synthesis of 2-(5"-(perfluorohexyl)-2,2':5', 2"-terthiophene-5-yl)-5-butyl-5H-thieno[3,2-c]pyrrole-4,6-dione, 8

To a refluxing toluene solution (8 ml) of Pd(AsPh$_3$)$_4$ (8 mol %, in situ prepared) and compound 4 (0.237 mmol) under N$_2$ atmosphere, compound 7 (0.26 mmol) diluted in 0.5 ml of toluene was added dropwise. The solution was refluxed for 8 h, then the solvent was removed under vacuum. The crude was purified by flash chromatography on silica gel, eluent DCM, followed by crystallization from toluene.

Compound 8 was obtained as an orange powder (74% yield). M.p. 182° (K→LC), 320° C. (LC→I), MS (70 eV, EI): m/z 773 (M.$^{+1}$). $^1$H NMR (CDCl$_3$, TMS/ppm) δ: 7.36 (d, $^3$J=3.6 Hz 1 H), 7.31 (s, 1H), 7.25 (d, $^3$J=4.4 Hz 1H), 7.17 (m, 4H), 3.61 (t, 2H), 1.63 (m, 2H), 1.36 (m, 2H), 0.95 (t, 3H). $^{13}$C NMR (CDCl$_3$, TMS/ppm): 163.9, 162.7, 149.5, 145.3, 141.8, 138.3, 137.5, 136.7, 135.1, 134.3, 131.1, 126.8, 126.1, 125.4, 125.0, 123.7, 116.5, 38.4, 30.8, 20.0, 13.6. $^{19}$F NMR) (CDCl$_3$, C$_6$H$_5$F/ppm): −80.2 (t, 3F), −100.8 (m, 2F), −121.0 (m, 4F), −122.3 (broad singlet, 2F), −125.6 (m, 2F). Anal. Calcd for C$_{28}$H$_{16}$F$_{13}$NO$_2$S$_4$ (773.67): C, 43.47; H, 2.08. Found: C, 43.52; H, 2.02.

The DSC thermograms of compound 8 (second run, 10° C./min) in air were obtained. Compound 8 shows a crystal-liquid transition at about 100° C. (not reversible), followed by a transition to isotropic phase at 297° C.

Optical spectroscopy of compound 8 was performed. FIG. 7(a) shows the absorption and emission spectra of compound 8 in CH$_2$Cl$_2$ solution and FIG. 7(b) the absorption and emission spectra of compound 8 as a vacuum sublimed film of 30 nm thickness.

CVs of compound 8 (1.1 mmol l$^{-1}$) at 100 mV/s in CH$_2$Cl$_2$, 0.1 ml l$^{-1}$ (C$_4$H$_9$)$_4$NClO$_4$ is shown in FIG. 8. The voltammogram of compound 8 shows a quasi-reversible reduction wave at E°$_{red1}$=−1.24 V, and an irreversible reduction wave at E$^{1/2}_{red2}$=−1.58 V. Oxidation waves are shown E°$_{ox1}$=−1.29 V and E°$_{ox2}$=−1.63 V.

Table 3 reports a summary of the optoelectronic properties measured for compound 8.

TABLE 3

| Comp. | $\lambda_{abs}$ nm$^a$ (theor) | $\lambda_{PL}$ nm$^a$ | $E_g^{opt}$ eV | $\lambda_{abs}$ Film$^b$ (nm) | $\lambda_{PL}$ film$^b$ (nm) | HOMO eV$^c$(theor)$^c$ | LUMO eV$^c$(theor) | $E_g^{ec}$ eV |
|---|---|---|---|---|---|---|---|---|
| Compound 8 | 433 (437) | 580 | 2.83 | 361 | 580 | −5.99 (−5.43) | −3.42 (−2.47) | 2.57 |

$^a$in CH$_2$Cl$_2$,
$^b$30 nm thick film,
$^c$E$_{HOMO}$ = e (4.68 − E$^0_{ox}$); E$_{LUMO}$ = e (4.68 − E$^0_{red}$)
Single crystal XRD were registered for compound 8.

X-ray data were collected using a Bruker SMART Apex II CCD area detector diffractometer with Mo—Kα (λ=0.71073 Å) as the incident radiation. Structures were solved using SIR 97 and were refined by full-matrix least-squares on F$_o^2$ using SHELXL97.

Crystal data for compound 8 were the following: C$_{28}$H$_{16}$F$_{13}$NO$_2$S$_4$, M=773.66, monoclinic, C2/c, a=109.92 (2), b=5.7796(11), c=19.480(4) Å, β=97.866(3)°, V=12259. (4) Å$^3$, Z=16, D$_c$=1.677 g cm$^{-3}$, μ=0.419 mm$^{-1}$, T=293 K, λ(Mo—Kα)=0.71073 Å, data/parameters=10695/874, converging to R$_1$=0.1401, wR$_2$=0.3803 (on 4941 I>2σ(I) observed data); R$_1$=0.2049, wR$_2$=0.4287 (all data), residual electron density: 1.299 e Å$^3$.

FIG. 9(a) shows the crystal structure of compound 8, as derived from the above described single crystal XRD analysis. FIG. 9(b) shows herringbone-like packing view down the b axis; and FIG. 9(c) shows herringbone-like packing view down the long molecular axis; wherein the H atoms the perfluorohexyl and n-butyl chain have been removed for clarity.

FIG. 10 is a 2D atomic force microscope image showing the morphology of a 30 nm thick layer of compound 8, grown on a 450 nm thick layer of PMMA which is deposited on a ITO layer.

EXAMPLE 5

Fabrication and Optoelectronic Measurements of Field Effect Transistor (OFET)

Organic thin film transistors were fabricated in bottom gate-top contact geometry. An ITO substrate was cleaned be means of two sonication cycles, in acetone first and 2-isopropanol then, for 10 minutes each. Then a 450 nm thick dielectric layer of PMMA was deposited by spin-coating on top of the clean ITO substrate. The relative electric permittivity ∈ was 3.6 at 100 Hz. The PMMA layer was then thermally annealed in a glove box at 120° C. (i.e., around 10° C. above the glass transition temperature for PMMA) for 15 hours under inert atmosphere. (CPMMA=7.08 nF/cm$^2$).

Then, an organic thin film layer consisting of compound 8 was grown on the top of said dielectric layer by vacuum sublimation in a vacuum chamber, with a deposition rate of 0.1 Å/s, at a base pressure of $10^{-6}$ mbar. The substrate temperature during the film deposition was kept at room temperature (RT).

Then, gold drain and source electrodes were made on top of the organic thin film by evaporation through a shadow mask. The thickness of said gold drain and source electrodes was 50 nm, while the channel length (L) and the channel width (W) were 70 μm and 12 mm, respectively.

The electrical characteristics of such a transistor were then measured. All opto-electronic measurements were carried out in an MBraun nitrogen glove box using a standard SUSS Probe Station equipped with a Hamamatsu photodiode for light detection.

The mobility values in saturation were calculated as described with reference to example 2.

FIG. 11(a) shows the output curve of such transistor comprising an organic layer consisting of compound 8. FIG. 11(b) shows the transfer curve of such transistor comprising an organic layer consisting of compound 8.

EXAMPLE 6

Fabrication and Optoelectronic Measurements of Organic Light Emitting Transistor (OLET)

An organic light emitting transistor was fabricated as described in example 3.

FIG. 12(a) shows the schematic structure of the obtained OLET device comprising a semiconductor layer formed of compound 8.

The electrical characteristics of such a transistor were then measured with the same methods as for example 2, and opto-electronic transfer curves obtained are shown in FIG. 12(b) together with the electroluminescence profile. FIG. 12(c) shows an optical microscope image of a working OLET based on compound 8. The luminescence stripe moves along the device channel.

Table 4 reports a summary of the electrical parameters measured for a 30 nm layer formed of compound 8 in an OLET device.

| Comp. | $\mu_h$ (cm$^2$V$^{-1}$s$^{-1}$) | $V_T^P$/V | $I_{on}/I_{off}$ | $\mu_e$ (cm$^2$V$^{-1}$s$^{-1}$) | $V_T^N$/V | OLET emission power (nW) |
|---|---|---|---|---|---|---|
| comp. 8 | $1.4 \times 10^{-5}$ | −39.5 | $10^4$ | 0.011 | 19.1 | 50 |

EXAMPLE 7

Synthesis of 2-(5''-(1,3-dioxolan-2-yl)-[2,2';5',2''-terthiophen]-5-yl)-5-hexyl-4H-thieno[2,3-c]pyrrole-4,6(5H)-dione

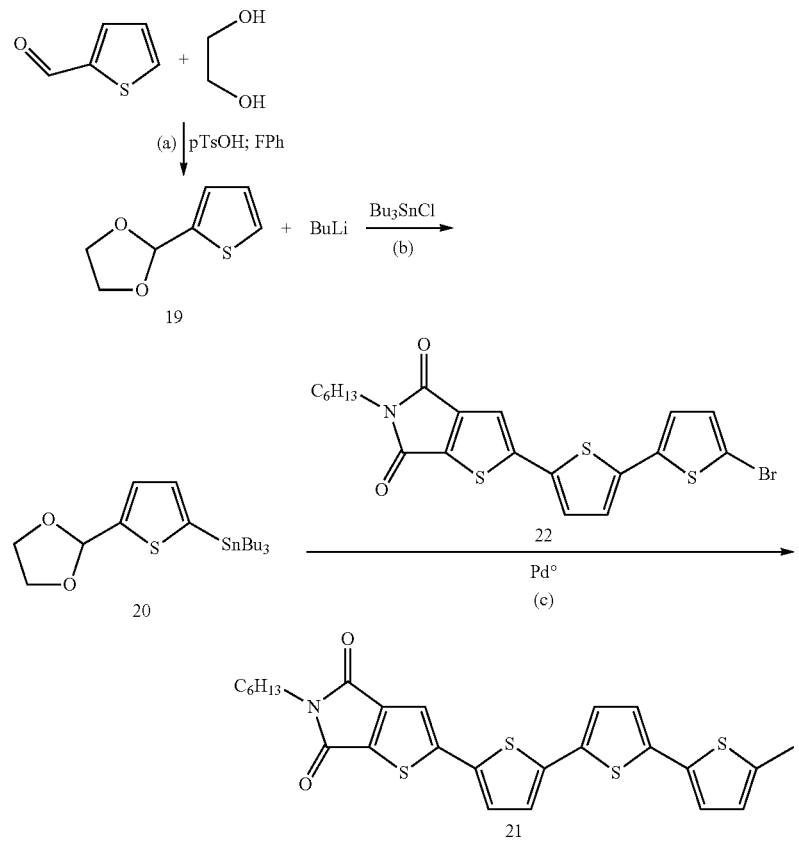

Step a): Synthesis of 2-(thiophen-2-yl)-1,3-dioxolane, 19

A mixture of thiophene-2-carbaldehyde (1 g, 0.0089 mol), ethylene glycol (1.3 g, 0.02 mol), p-TsOH (0.022 g), in 9 ml of fluorobenzene was stirred at reflux temperature under $H_2O$ separation for 5 h. Distillation at 55° C. (0.1 mmHg) gave 1.06 g of 19 as an oil (76% yield).

$^1$H NMR (CDCl$_3$, TMS/ppm) δ 7.33 (m, 1H), 7.17 (m, 1H), 7.04 (d, $^3$J=4.0 Hz, 2H), 6.00 (dd, $^3$J=3.6 Hz, $^3$J=3.2 Hz, 1H), 6.12 (s, 1H), 4.14 (m, 2H), 4.02 (m, 2H).

Step b): Synthesis of (5-(1,3-dioxolan-2-yl)thiophen-2-yl)tributylstannane, 20

To an anhydrous solution of 19 (0.970 g, 0.0062 mol) in 15 ml of THF, BuLi (2.5 M in hexane) (3.0 ml, 0.0074 mol) was added dropwise at −78° C. under N$_2$ atmosphere. The mixture was stirred for 2 h and then, at the same temperature, Bu$_3$SnCl (2.0 g, 0.0062 mol) was added dropwise. The reaction was left under stirring at room temperature overnight. The solvent was removed under vacuum and then the crude product was dissolved in ethyl ether and quenched with water. After extraction, the organic phase was dried over Na$_2$SO$_4$ and the solvent was evaporated, obtaining compound 20 as a brown oil (2.7 g, yield=98%).

$^1$H NMR (CDCl$_3$, TMS/ppm) δ 7.27 (d, $^3$J=3.2 Hz, 1H), 7.05 (d, $^3$J=3.2 Hz, 1H), 6.15 (s, 1H), 4.15 (m, 2H), 4.01 (m, 2H), 1.55 (m, 6H), 1.31 (m, 6H), 1.08 (m, 6H), 0.89 (t, 9H).

Step c): Synthesis of 2-(5″-(1,3-dioxolan-2-yl)-[2,2′:5′,2″-terthiophen]-5-yl)-5-hexyl-4H-thieno[2,3-c]pyrrole-4,6(5H)-dione, 21

To a refluxing toluene solution (3 ml) of 22 (100 mg, 0.2 mmol) and in-situ prepared catalyst Pd(AsPh$_3$)$_4$ (8 mol %, i.e. 8 mg of Pd$_2$dba$_3$ and 19 mg of AsPh$_3$ in 4 ml toluene) under N$_2$ atmosphere, 20 (102 mg, 0.23 mmol) in toluene (1 ml), was added dropwise. The solution was refluxed for 12 h then the solvent was evaporated and the crude product washed with pentane. The solid obtained was purified by flash chromatography on silica gel (elution with CH$_2$Cl$_2$). The fractions containing the product were combined, the solvent evaporated, and the residue crystallized from hot toluene to give an orange-red solid (60 mg, yield=54%).

M.p. 190° C. ELMS m/z 555 (M·$^+$). $\lambda\dagger_{max}$ (CH$_2$Cl$_2$), 439 nm, $\lambda\dagger_{em}$ (CH$_2$Cl$_2$), 604 nm.

$^1$H NMR (CDCl$_3$, TMS/ppm) δ 7.30 (s, 1 H), 7.24 (d, $^3$J=4.0 Hz, 1H), 7.13 (d, $^3$J=4.0 Hz, 1H), 7.12 (d, $^3$J=4.0 Hz, 1H), 7.09 (d, $^3$J=4.0 Hz, 1H), 7.07 (d, $^3$J=4.0 Hz, 1H), 7.06 (d, $^3$J=4.0 Hz, 1H), 6.09 (s, 1H), 4.15 (m, 2H), 4.04 (m, 2H), 3.60 (t, 2H) 1.64 (m, 2H), 1.31 (m, 6H), 0.88 (t, 3H).

$^{13}$C NMR (CDCl$_3$, TMS/ppm) δ 163.9, 162.8, 149.7, 145.2, 141.2, 138.8, 137.6, 137.2, 137.1, 135.1, 133.7, 127.0, 126.8, 125.3, 124.7, 124.5, 123.6, 116.3, 100.1, 65.3, 38.6, 31.4, 28.8, 26.5, 22.5, 14.0.

The invention claimed is:

1. A compound having formula (IIa)

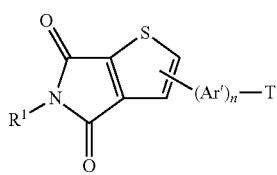

formula (IIa)

wherein:

n is an integer between 1 and 50;

Ar' is:

a unit selected from the group consisting of the following units (a), (b), (c), (d), (e), (f), (g), (h), (i), (l), (m), (k), (o), (p), (q), and (r):

(a)

(b)

(c)

(d)

(e)

(f)

(g)

-continued

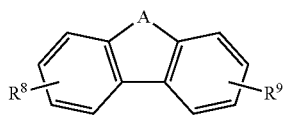
(h)

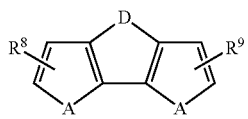
(i)

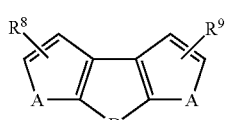
(l)

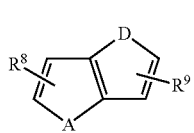
(m)

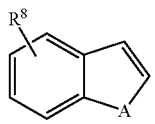
(n)

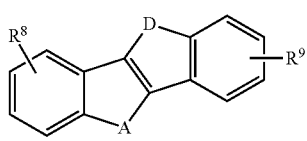
(o)

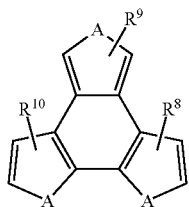
(p)

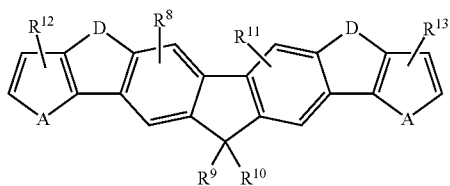
(q)

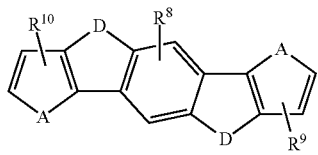
(r)

wherein A is selected from the group consisting of S, O Se, atoms and SO, $SO_2$, $R^{14}$—P=O, P—$R^{14}$, N—$R^{15}$, and $Si(R^{15})_2$ groups;

D is selected from the group consisting of C, S, O Se, atoms and SO, $SO_2$, $R^{14}$—P=O, P—$R^{14}$, $BR^{14}$, N—$R^{15}$, and $Si(R^{15})_2$ groups;

B, C, independently of each other, are selected from the group consisting of C, and N atoms;

E is selected from the group consisting of $C(R^{15})_2$, S, O, and $NR^{15}$ group;

$R^8$, $R^9$, $R^{10}$, $R^{11}$, $R^{12}$ and $R^{13}$, independently of each other, are selected from the group consisting of hydrogen, halogens, $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ linear or branched heteroalkyl groups, $C_2$-$C_{20}$ linear or branched heteroalkenyl groups, $C_2$-$C_{20}$ linear or branched heteroalkynyl groups, $C_3$-$C_{20}$ linear or branched cycloalkyl groups, $C_2$-$C_{20}$ linear or branched heterocycloalkyl groups, $C_2$-$C_{20}$ linear or branched alkylcarboxylic groups, $C_2$-$C_{20}$ linear or branched alkylcarboxamide groups, $C_2$-$C_{20}$ linear or branched alkylimino groups, $C_1$-$C_{20}$ linear or branched alkylsulphonic groups, $C_1$-$C_{20}$ linear or branched nitrile groups, $C_5$-$C_{40}$ aryl groups, and $C_6$-$C_{40}$ alkylaryl groups;

$R^{14}$, $R^{15}$ independently of each other, are selected from the group consisting of hydrogen, $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ linear or branched heteroalkyl groups, $C_2$-$C_{20}$ linear or branched heteroalkenyl groups, $C_2$-$C_{20}$ linear or branched heteroalkynyl groups, $C_3$-$C_{20}$ linear or branched cycloalkyl groups, $C_2$-$C_{20}$ linear or branched heterocycloalkyl groups, $C_2$-$C_{20}$ linear or branched alkylcarboxylic groups, $C_2$-$C_{20}$ linear or branched alkylcarboxamide groups, $C_2$-$C_{20}$ linear or branched alkylimino groups, $C_1$-$C_{20}$ linear or branched alkylsulphonic groups, $C_2$-$C_{20}$ linear or branched nitrile groups, $C_5$-$C_{40}$ aryl groups, $C_1$-$C_{40}$ heteroaryl groups, and $C_6$-$C_{40}$ alkylaryl groups; or the [Ar']$_n$ unit is selected from the group consisting of the following groups (s) and (t):

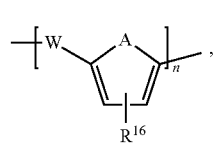
(s)

and

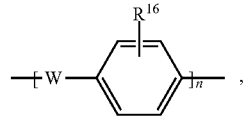
(t)

wherein A is as defined above;

W is a moiety selected from the group consisting of the above defined units (a), (b), (c), (d), (e), (f), (g), (h), (i), (l), (m), (n), (o), (p), (q), and (r); and $R^{16}$ is selected from the group consisting of the group consisting of hydrogen, halogens, $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ linear or branched heteroalkyl groups, $C_2$-$C_{20}$ linear or branched heteroalkenyl groups, $C_2$-$C_{20}$ linear or branched heteroalkynyl groups, $C_3$-$C_{20}$ linear or branched cycloalkyl groups, $C_2$-$C_{20}$ linear or branched heterocycloalkyl groups, $C_2$-$C_{20}$ linear or branched alkylcarboxylic groups, $C_2$-$C_{20}$ linear or branched alkylcarboxamide groups, $C_2$-$C_{20}$ linear or branched alkylimino groups, $C_1$-$C_{20}$ linear or branched alkylsulphonic groups, $C_1$-$C_{20}$ linear or branched nitrile groups, $C_5$-$C_{40}$ aryl groups, $C_1$-$C_{40}$ heteroaryl groups, and $C_6$-$C_{40}$ alkylaryl groups; or the [Ar']$_n$ unit is selected from the group consisting of following formulas (u), (v), (w), (x) and (y):

(u)
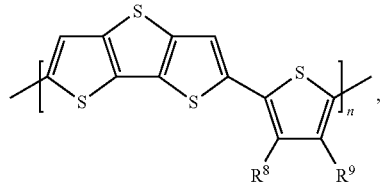

(v)
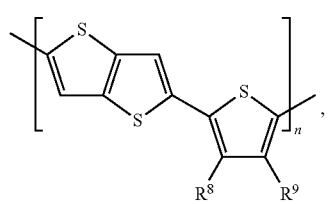

(w)
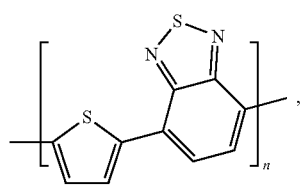

-continued (x)
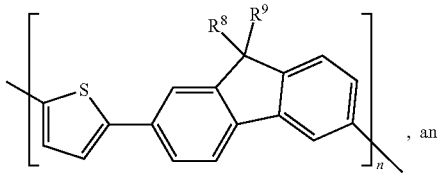
, and (y)
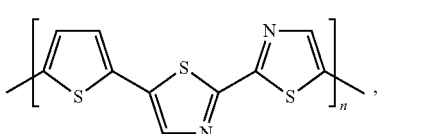

wherein n is comprised between 2 and 10 and $R^8$, $R^9$ are as defined above;

T is selected from the group consisting of $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ fluoroalkyl groups, $C_1$-$C_{20}$ thioalkyl groups, $C_1$-$C_{20}$ silicioalkyl groups, $C_1$-$C_{20}$ alkylamino groups, $C_2$-$C_{20}$ alkylimino groups, phenyl groups, phenyl groups substituted with at least one $C_1$-$C_{10}$ alkyl group and/or with at least one $C_1$-$C_{10}$ heteroalkyl groups, thienyl group, thienyl groups substituted with at least one $C_1$-$C_{10}$ alkyl group and/or with at least one $C_1$-$C_{10}$ heteroalkyl groups, naphthalene, substituted naphthalene, antracene, substituted antracene, and $C_4$-$C_{20}$ triciclic heteroaryl groups, and $R^1$ is selected from the group consisting of $C_1$-$C_{40}$ linear and branched alkyl groups.

2. The compound according to claim 1, wherein said compound is selected from the group consisting of the following compounds 6, 8, 9, 10, 11, 12, 13, 14, 15, 16, 17, and 18:

compound 6
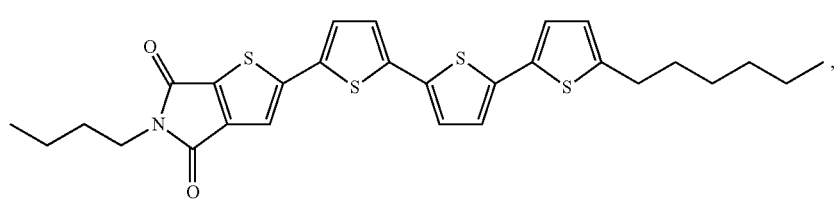

compound 8
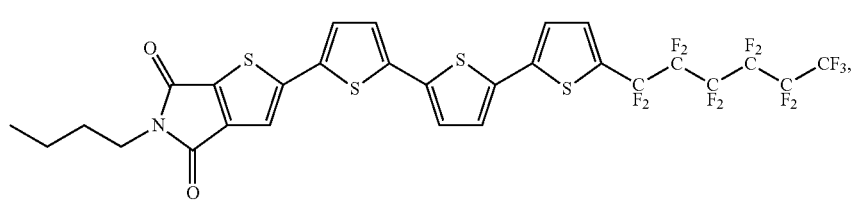

compound 9
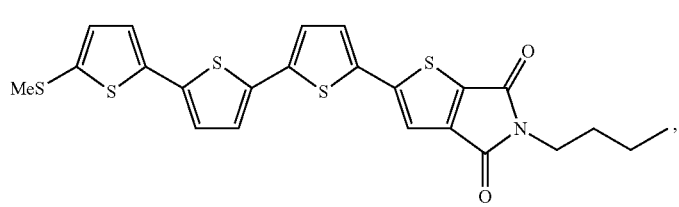

-continued
compound 10
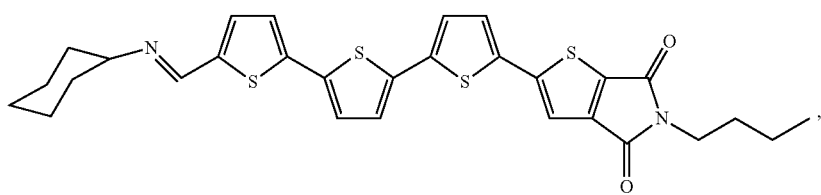
compound 11
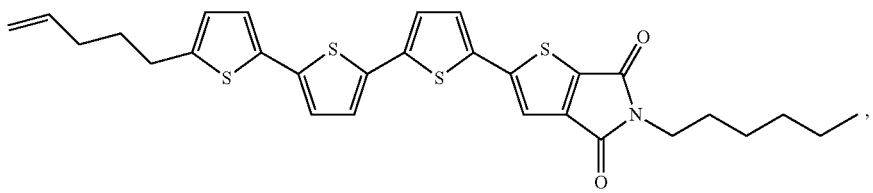
compound 12
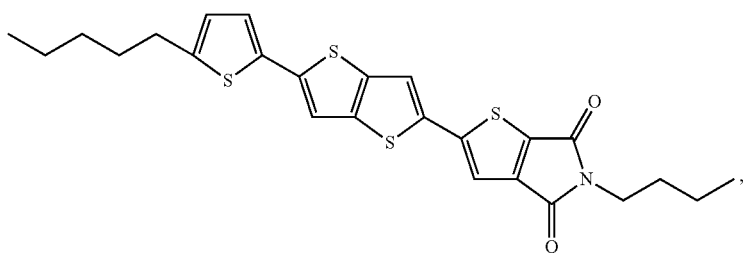
compound 13
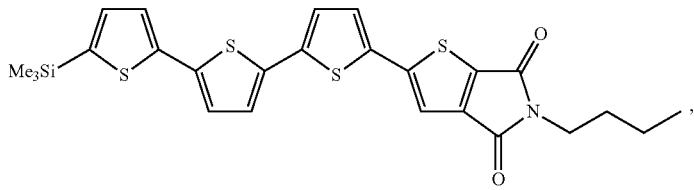
compound 14
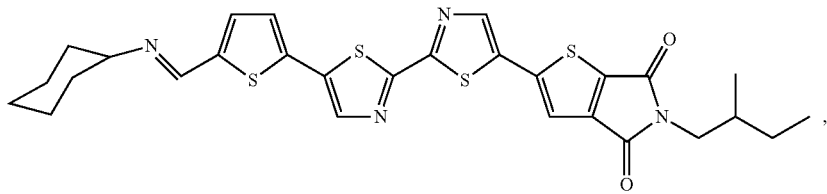
compound 15
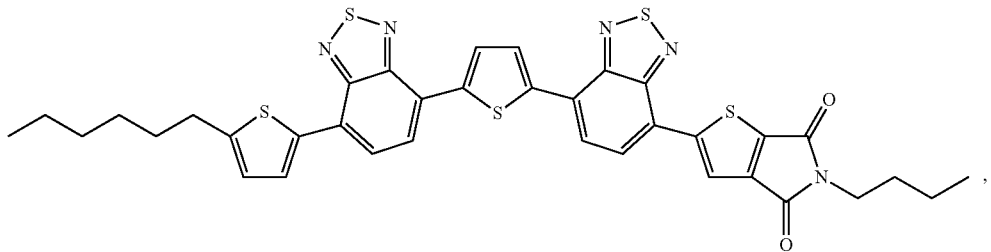
compound 16
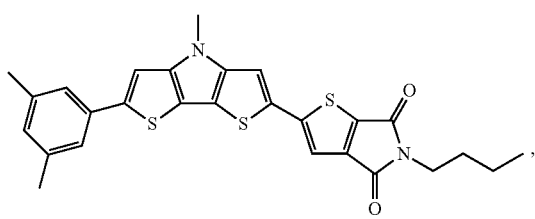
compound 17
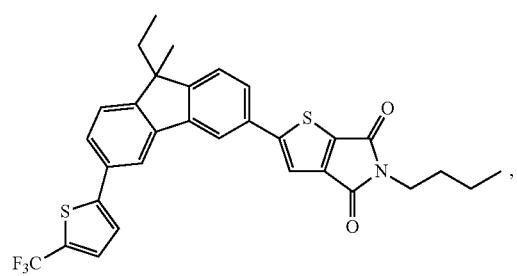
and compound 18

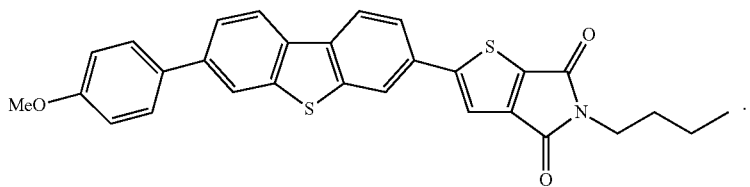

3. An electronic device comprising the compound according to claim 1 as an organic semiconductor material.

4. The electronic device according to claim 3, wherein the organic semiconductor material is an n-type organic semiconductor material.

5. An electronic device comprising a semiconductor layer in contact with a number of electrodes, wherein the semiconductor layer includes at least one compound according claim 1.

6. A compound having formula (Ia)

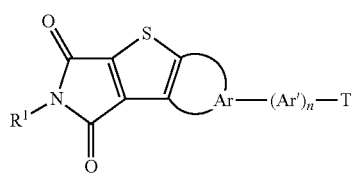

formula (Ia)

wherein:
n is an integer between 1 and 50;
Ar is selected from the group consisting of the following rings (α), (β), (γ), (δ), (ε), (ζ), (η), (θ), and (ι):

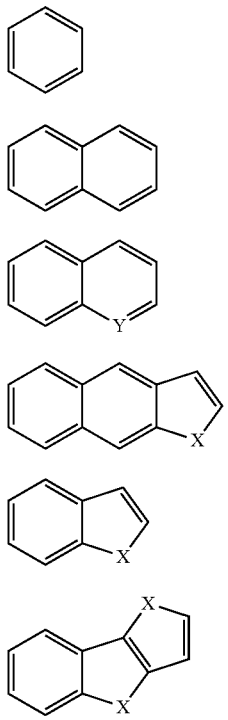

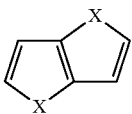

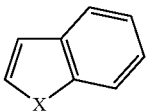

wherein X is selected from the group consisting of S, SO, $SO_2$, O, Si, Se, and $NR^{17}$, Y is selected from the group consisting of C and N;

$R^{17}$ is selected from the group consisting of hydrogen, $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ linear or branched heteroalkyl groups, $C_2$-$C_{20}$ linear or branched heteroalkenyl groups, $C_2$-$C_{20}$ linear or branched heteroalkynyl groups, $C_3$-$C_{20}$ linear or branched cycloalkyl groups, $C_2$-$C_{20}$ linear or branched heterocycloalkyl groups, $C_2$-$C_{20}$ linear or branched alkylcarboxylic groups, $C_2$-$C_{20}$ linear or branched alkylcarboxamide groups, $C_2$-$C_{20}$ linear or branched alkylimino groups, $C_1$-$C_{20}$ linear or branched alkylsulphonic groups, $C_1$-$C_{20}$ linear or branched nitrile groups, $C_5$-$C_{40}$ aryl groups, $C_1$-$C_{40}$ heteroaryl groups, and $C_6$-$C_{40}$ alkylaryl groups;

Ar' is:
a unit selected from the group consisting of the following units (a), (b), (c), (d), (e), (f), (g), (h), (i), (l), (m), (k), (o), (p), (q), and (r):

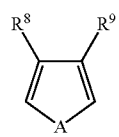

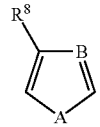

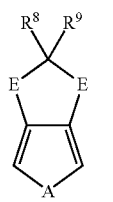 (c)

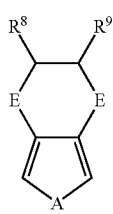 (d)

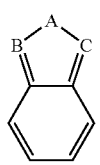 (e)

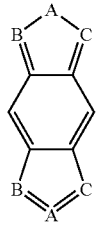 (f)

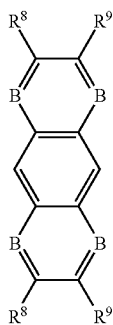 (g)

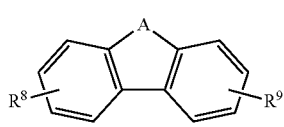 (h)

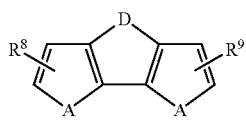 (i)

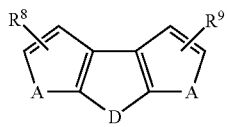 (l)

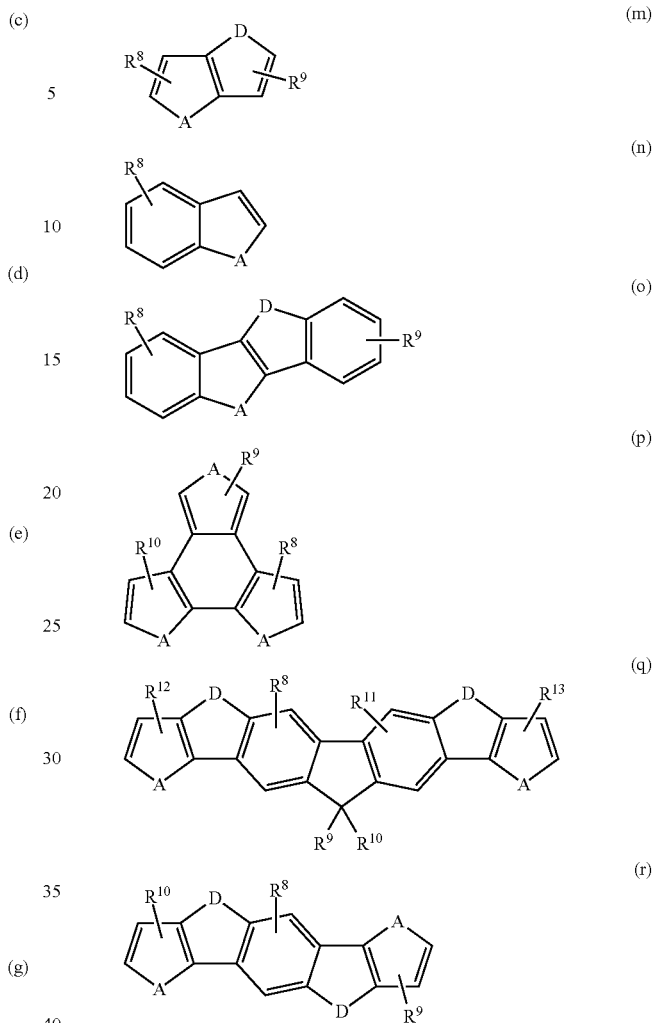

wherein A is selected from the group consisting of S, O, and Se atoms and SO, $SO_2$, $R^{14}$—P=O, P—$R^{14}$,N—$R^{15}$, and $Si(R^{15})_2$ groups;

D is selected from the group consisting of C, S, O, Se, atoms and SO, $SO_2$, $R^{14}$—P=O, P—$R^{14}$,$BR^{14}$,N—$R^{15}$, and $Si(R^{15})_2$ groups;

B, C, independently of each other, are selected from the group consisting of C, and N atoms;

E is selected from the group consisting of $C(R^{15})_2$, S, O, and $NR^{15}$ group;

$R^8$, $R^9$, $R^{10}$, $R^{11}$, $R^{12}$ and $R^{13}$, independently of each other, are selected from the group consisting of hydrogen, halogens, $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ linear or branched heteroalkyl groups, $C_2$-$C_{20}$ linear or branched heteroalkenyl groups, $C_2$-$C_{20}$ linear or branched heteroalkynyl groups, $C_3$-$C_{20}$ linear or branched cycloalkyl groups, $C_2$-$C_{20}$ linear or branched heterocycloalkyl groups, $C_2$-$C_{20}$ linear or branched alkylcarboxylic groups, $C_2$-$C_{20}$ linear or branched alkylcarboxamide groups, $C_2$-$C_{20}$ linear or branched alkylimino groups, $C_1$-$C_{20}$ linear or branched alkylsulphonic groups, $C_1$-$C_{20}$ linear or branched nitrile groups, $C_5$-$C_{40}$ aryl groups, and $C_6$-$C_{40}$ alkylaryl groups;

$R^{14}, R^{15}$ independently of each other, are selected from the group consisting of hydrogen, $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ linear or branched heteroalkyl groups, $C_2$-$C_{20}$ linear or branched heteroalkenyl groups, $C_2$-$C_{20}$ linear or branched heteroalkynyl groups, $C_3$-$C_{20}$ linear or branched cycloalkyl groups, $C_2$-$C_{20}$ linear or branched heterocycloalkyl groups, $C_2$-$C_{20}$ linear or branched alkylcarboxylic groups, $C_2$-$C_{20}$ linear or branched alkylcarboxamide groups, $C_2$-$C_{20}$ linear or branched alkylimino groups, $C_1$-$C_{20}$ linear or branched alkylsulphonic groups, $C_2$-$C_{20}$ linear or branched nitrile groups, $C_5$-$C_{40}$ aryl groups, $C_1$-$C_{40}$ heteroaryl groups, and $C_6$-$C_{40}$ alkylaryl groups; or the $[Ar']_n$ unit is selected from the group consisting of the following groups (s) and (t):

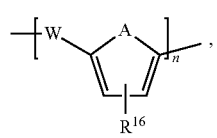
(s)

and

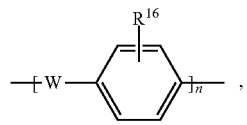
(t)

wherein A is as defined above;

W is a moiety selected from the group consisting of the above defined units (a), (b), (c), (d), (e), (f), (g), (h), (i), (l), (m), (n), (o), (p), (q), and (r); and $R^{16}$ is selected from the group consisting of the group consisting of hydrogen, halogens, $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ linear or branched heteroalkyl groups, $C_2$-$C_{20}$ linear or branched heteroalkenyl groups, $C_2$-$C_{20}$ linear or branched heteroalkynyl groups, $C_3$-$C_{20}$ linear or branched cycloalkyl groups, $C_2$-$C_{20}$ linear or branched heterocycloalkyl groups, $C_2$-$C_{20}$ linear or branched alkylcarboxylic groups, $C_2$-$C_{20}$ linear or branched alkylcarboxamide groups, $C_2$-$C_{20}$ linear or branched alkylimino groups, $C_1$-$C_{20}$ linear or branched alkylsulphonic groups, $C_1$-$C_{20}$ linear or branched nitrile groups, $C_5$-$C_{40}$ aryl groups, $C_1$-$C_{40}$ heteroaryl groups, and $C_6$-$C_{40}$ alkylaryl groups; or the $[Ar']_n$ unit is selected from the group consisting of following formulas (u), (v), (w), (X) and(y):

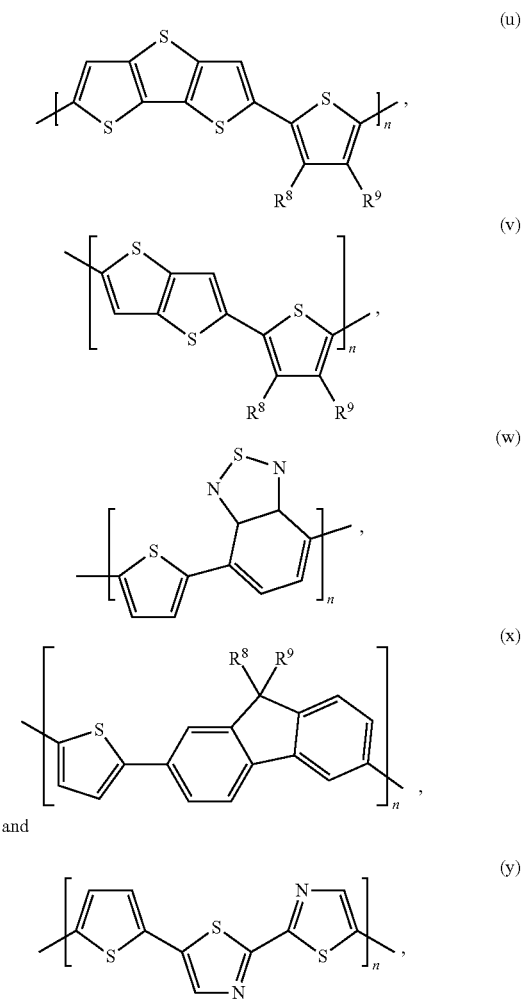

wherein n is comprised between 2 and 10 and $R^8$, $R^9$ are as defined above;

T is selected from the group consisting of $C_1$-$C_{20}$ linear or branched alkyl groups, $C_2$-$C_{20}$ linear or branched alkenyl groups, $C_2$-$C_{20}$ linear or branched alkynyl groups, $C_1$-$C_{20}$ fluoroalkyl groups, $C_1$-$C_{20}$ thioalkyl groups, $C_1$-$C_{20}$ silicioalkyl groups, $C_1$-$C_{20}$ alkylamino groups, $C_2$-$C_{20}$ alkylimino groups, phenyl groups, phenyl groups substituted with at least one $C_1$-$C_{10}$ alkyl group and/or with at least one $C_1$-$C_{10}$ heteroalkyl groups, thienyl group, thienyl groups substituted with at least one $C_1$-$C_{10}$ alkyl group and/or with at least one $C_1$-$C_{10}$ heteroalkyl groups, naphthalene, substituted naphthalene, antracene, substituted antracene, and $C_4$-$C_{20}$ triciclic heteroaryl groups, and $R^1$ is selected from the group consisting of $C_1$-$C_{40}$ linear and branched alkyl groups.

* * * * *